(12) United States Patent
Vinayagamoorthy

(10) Patent No.: US 10,351,899 B2
(45) Date of Patent: Jul. 16, 2019

(54) METHODS FOR DETECTING NUCLEIC ACID FRAGMENTS

(71) Applicant: Bio-ID Diagnostic Inc., Edmonton (CA)

(72) Inventor: Thuraiayah Vinayagamoorthy, Charlotte, NC (US)

(73) Assignee: Bio-ID Diagnostics Inc., Saskatoon, Saskatchewan (CA)

( * ) Notice: Subject to any disclaimer, the term of this patent is extended or adjusted under 35 U.S.C. 154(b) by 209 days.

(21) Appl. No.: 15/025,223

(22) PCT Filed: Sep. 25, 2014

(86) PCT No.: PCT/CA2014/050918
§ 371 (c)(1),
(2) Date: Mar. 25, 2016

(87) PCT Pub. No.: WO2015/042708
PCT Pub. Date: Apr. 2, 2015

(65) Prior Publication Data
US 2017/0166954 A1    Jun. 15, 2017

Related U.S. Application Data

(60) Provisional application No. 61/882,540, filed on Sep. 25, 2013.

(51) Int. Cl.
| | | |
|---|---|---|
| C12P 19/34 | (2006.01) |
| C12Q 1/6806 | (2018.01) |
| C12Q 1/6858 | (2018.01) |
| C12Q 1/6886 | (2018.01) |
| C12Q 1/6853 | (2018.01) |

(52) U.S. Cl.
CPC ......... *C12Q 1/6806* (2013.01); *C12Q 1/6853* (2013.01); *C12Q 1/6858* (2013.01); *C12Q 1/6886* (2013.01); *C12Q 2600/156* (2013.01)

(58) Field of Classification Search
None
See application file for complete search history.

(56) References Cited

U.S. PATENT DOCUMENTS

2007/0077582 A1* 4/2007 Slepnev ............... C12Q 1/6851
 435/6.11
2009/0023151 A1* 1/2009 Dawson ............... C12Q 1/6813
 435/6.16

* cited by examiner

*Primary Examiner* — Kenneth R Horlick

(57) ABSTRACT

Provided are methods for detecting and analyzing polynucleotides in a biological sample or sample derived therefrom for example, using a synthetic template polynucleotide. In some aspects, a target polynucleotide in the sample hybridizes to the template polynucleotide and is extended by a polymerase, generating an extended target polynucleotide. In some examples, the extended target polynucleotide is amplified, for example, by polymerase chain reaction, and sequences of the target polynucleotide determined, for example, by priming in the region of the extended target polynucleotide generated by extension and sequencing towards the region having identity to the target polynucleotide. In some aspects, the target polynucleotide is thereby detected in the sample and its sequence identified. In some aspects, the provided methods can be used to capture polynucleotide fragments in a biological sample, for example, plasma, and determine respective biomarkers they carry, for example, for cancer diagnosis and prognosis.

8 Claims, 10 Drawing Sheets

Specification includes a Sequence Listing.

5'-TTTTGGTCTAGCTACAGTGAAATCTGATGGAGTGGGTCCATCAGTTTGAACAGT-3' (SEQ ID NO: 4)
3'-CTGGAGTGTCATTTTATCCACTAAAACCAGATCGATGTCACTTTAGAGCTACCTCACCCAGGGTAGTCAAACTTGTCAACAGACCTAGGTA
AAACACCTACCATTCTTAACTCC-5' (SEQ ID NO: 1)

B.

5'-GACCTCACATGTAAATAGGTGATTTTGGTCTAGCTACAGAGAAATC-3' (SEQ ID NO: 2)
3'-CTGGAGTGTCATTTTATCCACTAAAACCAGATCGATGTCTCTTTAGAGCTACCTCACCCAGGGTAGTCAAACTTGTCAACAGACCTAGGTA
AAACACCTACCATTCTTAACTCC-5' (SEQ ID NO: 8)

C.

5'-TTTTGGTCTAGCTACAGAGAAATCTCGATGGAGTGGGTCCATCAGTTTGAACAGT-3' (SEQ ID NO: 3)
3'-CTGGAGTGTCATTTTATCCACTAAAACCAGATCTCTTTAGAGCTACCTCACCCAGGGTAGTCAAACTTGTCAACAGACCTAGGTA
AAACACCTACCATTCTTAACTCC-5' (SEQ ID NO: 8)

SEQUENCE LISTING

<160> NUMBER OF SEQ ID NOS: 8

<210> SEQ ID NO 1
<211> LENGTH: 115
<212> TYPE: DNA
<213> ORGANISM: Artificial Sequence

```
<220> FEATURE:
<223> OTHER INFORMATION: Synthetic Construct

<400> SEQUENCE: 1
cctcaattct taccatccac aaaatggatc cagacaactg ttcaaactga tgggacccac      60
tccatcgaga tttcactgta gctagaccaa aatcacctat ttttactgtg aggtc         115

<210> SEQ ID NO 2
<211> LENGTH: 47
<212> TYPE: DNA
<213> ORGANISM: Artificial Sequence
<220> FEATURE:
<223> OTHER INFORMATION: Synthetic Construct

<400> SEQUENCE: 2
gacctcacat gtaaaatagg tgattttggt ctagctacag agaaatc                   47

<210> SEQ ID NO 3
<211> LENGTH: 56
<212> TYPE: DNA
<213> ORGANISM: Artificial Sequence
<220> FEATURE:
<223> OTHER INFORMATION: Synthetic Construct

<400> SEQUENCE: 3
ttttggtcta gctacagaga aatctcgatg gagtgggtcc catcagtttg aacagt         56

<210> SEQ ID NO 4
<211> LENGTH: 56
<212> TYPE: DNA
<213> ORGANISM: Artificial Sequence
<220> FEATURE:
<223> OTHER INFORMATION: Synthetic Construct

<400> SEQUENCE: 4
ttttggtcta gctacagtga aatctcgatg gagtgggtcc catcagtttg aacagt         56

<210> SEQ ID NO 5
<211> LENGTH: 30
<212> TYPE: DNA
<213> ORGANISM: Artificial Sequence
<220> FEATURE:
<223> OTHER INFORMATION: Synthetic Construct

<400> SEQUENCE: 5
caattcttac catccacaaa atggatccag                                      30

<210> SEQ ID NO 6
<211> LENGTH: 32
<212> TYPE: DNA
<213> ORGANISM: Artificial Sequence
<220> FEATURE:
<223> OTHER INFORMATION: Synthetic Construct

<400> SEQUENCE: 6
aaactgatgg gacccactcc atcgagattt ct                                   32

<210> SEQ ID NO 7
<211> LENGTH: 32
<212> TYPE: DNA
<213> ORGANISM: Artificial Sequence
<220> FEATURE:
<223> OTHER INFORMATION: Synthetic Construct

<400> SEQUENCE: 7
```

```
aaactgatgg gacccactcc atcgagattt ca                              32

<210> SEQ ID NO 8
<211> LENGTH: 115
<212> TYPE: DNA
<213> ORGANISM: Artificial Sequence
<220> FEATURE:
<223> OTHER INFORMATION: Synthetic Construct

<400> SEQUENCE: 8
cctcaattct taccatccac aaaatggatc cagacaactg ttcaaactga tgggacccac   60
tccatcgaga tttctctgta gctagaccaa aatcacctat ttttactgtg aggtc        115
```

METHODS FOR DETECTING NUCLEIC ACID FRAGMENTS

This application is a U.S. National Stage of PCT/CA2014/050918, filed Sep. 25, 2014, which claims the benefit of priority to U.S. Provisional Application No. 61/882,540, filed Sep. 25, 2013, the contents of these applications are incorporated herein by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 761392000100_SeqList.txt, date recorded: Sep. 6, 2016, size: 1,945 bytes).

TECHNICAL FIELD

The present disclosure relates in some aspects to methods for capturing, amplifying, and/or detecting polynucleotides and determining polynucleotide sequences. For example, the methods are carried out in some aspects for the identification of biomarkers, e.g., genetic and epigenetic markers, such as in diagnosis and prognosis of diseases and conditions. The disclosure relates in some aspects to analysis of fragmented polynucleotides from a biological sample, e.g., a blood, plasma or serum sample, associated with or suspected to be associated with disease states, healthy states, or conditions such as neoplastic, pre-malignant or proliferative diseases or other genetic diseases, disorders, or conditions. In some aspects, the methods capture and make sufficient copies of the target polynucleotide or extension or copy thereof, so that a biomarker carried by the target polynucleotide can be identified by DNA sequencing and/or other methods. In some aspects, sequencing methods also are provided.

BACKGROUND

Biomarkers include genetic and epigenetic markers, such as mutations, deletions, insertions, rearrangements, and polymorphisms, including single nucleotide polymorphisms (SNP), copy number variations, biallelic polymorphisms, including multinucleotide changes, repeats, translocations, and epigenetic changes such as gene hypermethylation. Variations, including DNA mutations, can occur as the result of inherited (inborn) genetic errors or as acquired (somatic) mutations, resulting, for example, from environmental insults and the process of aging or disease process. For example, mutations in oncogenes and tumor suppressor genes can contribute to the predisposition, incidence, and progression of cancer. Thus, genetic and epigenetic variations can be markers of diseases or conditions. Available methods and assay systems for detecting and analyzing various biomarkers and for screening and diagnosis of cancer and other diseases and conditions, have not been entirely satisfactory. Methods and assay systems are needed for detecting and analyzing various biomarkers for screening, detecting, and diagnosing diseases and conditions, such as cancer, and monitoring corresponding therapeutic intervention, such as chemotherapy.

SUMMARY

Provided are methods and assay systems for detecting and analyzing biomarkers, such as genetic or epigenetic markers, e.g., genetic variations, mutations, deletions, insertions, allelic variations, wild-type or normal alleles, and epigenetic modifications, and for screening, detecting, and diagnosing various diseases and conditions, such as cancer. For example, provided are methods for detecting polynucleotide fragments that are present at very low concentrations and carry biomarkers, such as disease- or condition-associated markers, where the biomarkers and/or fragments are detected simultaneously in the presence of polynucleotides that do not contain the genetic markers, from various samples, including bodily fluids. Also provided are sequencing methods, e.g., for simultaneous detection of a plurality of biomarkers present at low copy number, in the presence of wild-type or normal polynucleotides, for example, in the same reaction.

In some aspects, the methods are capable of detecting multiple biomarkers simultaneously, for example, at very low (e.g., subclinical) concentrations, and/or in the presence of polynucleotides not containing the biomarkers (e.g., where the biomarker is a mutation or mutant allele, in the presence of wild-type polynucleotides or polynucleotides from normal cells). Typically, the methods detect the biomarkers in a biological sample (or a sample derived therefrom), such as a bodily fluid, for example, from a subject having or suspected of having a disease or condition or disorder. Among the provided are those that address certain challenges in detecting and sequencing nucleic acids from body fluids. For example, provided are methods capable of (a) detecting all or a plurality of mutations or other genetic variations associated with a particular disease or condition (e.g., six mutations associated with colon cancer), such as in the same reaction, and/or (b) detecting such mutations at sub-clinical concentrations (e.g., pre-malignancy or sub-clinical nodal metastases).

The provided methods are useful in some aspects in detecting fragmented polynucleotides, e.g., DNA, shed from intact cells within bodily fluids or other extracellular samples, such as in blood, urine, and stool. Fragmented polynucleotides, e.g. DNA are often found in such samples in small pieces and at low concentrations. In certain aspects, the provided methods can distinguish between polynucleotides containing the biomarker of interest and those that do not contain it that also are present in the bodily fluid or other sample. In some aspects, the ability to detect and determine sequence of such fragmented polynucleotides can provide important information regarding a disease or condition of interest, such as information regarding disease state, e.g., whether particular cancer-associated mutations are present. Hence, in some aspects, the provided methods are useful for identification of fragmented polynucleotides, e.g., DNA, for use in diagnosis, e.g., early diagnosis, prevention, and management of diseases and conditions.

In some embodiments, the methods address the challenge of the relatively small size of certain fragmented polynucleotides found, for example, at low or very low concentrations, in biological samples such as bodily fluids—which in part due to their size can be difficult to assess via conventional methods such as PCR and available detection methods, including sequencing methods. In one aspect, this challenge is met by using such small fragments (deemed "target polynucleotides") as primers in extension reactions, in which a template having a known sequence (e.g., a synthetic template) (deemed "template polynucleotide") is provided and serves as a basis for extension of the fragmented polynucleotide containing the biomarker or variation of interest. In a variation, the fragments are ligated based on the template.

Thus, in some embodiments, the methods include an extension reaction in which the fragmented polynucleotide, e.g., fragmented DNA present in the biological sample (deemed a "target polynucleotide") is used as a primer and is extended by a polymerase based on the sequence of a template polynucleotide, which is provided. In this aspect, the fragment (target polynucleotide) hybridizes to the template polynucleotide and is extended based on the sequence of the template polynucleotide. The product of such an extension (deemed an "extended target polynucleotide") is then optionally amplified and used (or the amplification product used) in a sequencing reaction to determine its sequence and ultimately detect the biomarker, e.g., genetic variation, in or from the sample. Thus, in some aspects, the provided methods are distinct from available methods in that they employ fragmented polynucleotides present in biological samples as the primers, rather than templates, in an extension reaction. Thus, the methods in some aspects allow for capture, amplification, and detection of small polynucleotide fragments, e.g., fragments of less than 200 or less than 100 nucleotides in length, which are not amenable to PCR and sequencing by certain available methods.

In some embodiments, the methods are carried out by (a) contacting a sample with a template polynucleotide, under conditions whereby one or more target polynucleotide in the sample hybridizes to the template polynucleotide, (b) producing an extended target polynucleotide, and (c) determining the nucleotide sequence of all or a portion of the extended target polynucleotide.

Typically, the polynucleotide (the "target polynucleotide") being assessed, e.g., sequenced, by the methods, contains or is suspected of containing a biomarker, such as a genetic or epigenetic marker. It often is unknown at the outset of the method whether the target polynucleotide and/or the sample contain the biomarker; thus, an outcome of the methods is often the detection of the presence or absence of the biomarker in the sample. In some aspects, using a fragmented polynucleotide as a primer (rather than a template) for extension is a distinguishing feature of the provided methods.

Thus, in some embodiments, the target polynucleotide contains a biomarker, which in some aspects is an entire gene or particular allelic (e.g., wild-type or mutant or variant) sequence, or a particular one or more residues thereof, mutation, SNP, insertion, allelic difference, deletion, methylation, demethylation, or other modification. In some aspects, the biomarker is a single residue, e.g., an allelic difference or point mutation compared to a corresponding wild-type sequence. In some aspects, the presence of the biomarker is unknown in the outset of the methods, such that the methods determine the presence of the biomarker in the sample. At the outset of the method, it may be suspected that the biomarker is present in the sample.

In some aspects, step (c) or a determining step includes determining the sequence of all or a portion of the extended target polynucleotide (or a copy thereof). In general, the sequence so-determined contains the biomarker of interest, such that the methods detect the presence or absence of the biomarker in the target polynucleotide and/or in the sample. In some aspects, the methods determine or detect the biomarker. Determining the sequence of all or the portion of the extended target polynucleotide can be carried out by determining a sequence of a copy thereof, such as following an amplification reaction.

In some aspects, the extended polynucleotide is generated by providing a polymerase under conditions that permit extension of the target polynucleotide by the polymerase, thereby producing the extended target polynucleotide. In such an aspect, the target polynucleotide serves as an extension primer in an extension reaction, generating the extended target polynucleotide based on the template polynucleotide. Typically, the template polynucleotide is designed or constructed in a way that does not allow its extension by the polymerase and/or is not extended by the polymerase.

In some embodiments, the extended target polynucleotide is generated by contacting the sample with the template polynucleotide under conditions whereby a first and a second target polynucleotides (at least one of which contains a biomarker) in the sample hybridize to the template polynucleotide and are ligated to one another, thereby forming the extended target polynucleotide.

The template polynucleotide in some aspects is longer in sequence than the target polynucleotide. In some aspects, one or more portions of the template polynucleotide are, or the template polynucleotide is, synthetic, a double or single stranded DNA, a single stranded DNA, a single stranded RNA, or a microRNA. In some aspects, the template polynucleotide is unable to be extended by a primer, for example, in some aspects is blocked at its 3' end or is circular, thereby preventing primer extension of the template polynucleotide. In some aspects, a plurality of template polynucleotides, each with complementarity to the target polynucleotide, are added to the sample. In one embodiment, one or more templates complementary to the biomarker and one or more templates complementary to a different marker, such as a corresponding wild-type sequence or residue, or different allelic variant or sequence not containing the biomarker or variation of interest, are used in parallel with a template polynucleotide containing a sequence complementary at the biomarker(s) of interest.

In some aspects, the template polynucleotide comprises a first segment that is hybridizable to the target polynucleotide and a second segment that does not hybridize to the target polynucleotide, or does not hybridize to the target polynucleotide under certain conditions, such as under stringent conditions or under conditions that allow hybridization of the first segment to the target polynucleotide. The second segment in certain aspects is 5' to the first, e.g., is located directly to the 5' of the first segment. In some examples, the extended target polynucleotide includes a portion complementary to the first segment and a portion complementary to the second segment.

In some aspects, the target polynucleotide is shorter in sequence than the template polynucleotide. In some aspects, the target polynucleotide is naturally occurring. In some aspects, the target polynucleotide includes a plurality of target polynucleotides, each comprising the biomarker. In some aspects, the target polynucleotide is a fragmented polynucleotide, such as a fragmented DNA. In some aspects, the target polynucleotide is between at or about 5 and at or about 1000 nucleotides in length, such as between at or about 5 and 200 nucleotides in length, e.g., between at or about 50-200, 5-100, 10-200, 10-100, or 10-50 nucleotides in length.

In some aspects, the determining step includes or is carried out by performing nucleotide sequencing, for example, on the extended target polynucleotide or a copy, e.g., an amplified copy, thereof.

Also among the provided embodiments are sequencing methods, which can be used in conjunction with others of the provided methods, e.g., the capture and amplification methods. In some aspects, such methods are capable of sequencing multiple different polynucleotides simultaneously, sequencing and detecting polynucleotides with biomarkers, e.g., genetic variations, at very low copy number, for example, as low as at or about 1 copy of the biomarker or target polynucleotide in or per 1,000, 10,000, 100,000, or 1,000,000 total number of polynucleotides, or total number of corresponding polynucleotides, for example, in the case of a mutant biomarker, total number corresponding number of corresponding wild-type polynucleotides, in the sample or biological sample from which the sample is derived. Corresponding polynucleotides in some aspects are those that contain identity or complementarity to the gene, region, or locus of interest (e.g., in the gene, region, or locus, in which the biomarker is found); in some aspects, the corresponding polynucleotides do not contain the biomarker of interest, such as in the case of a mutant or variant biomarker, a corresponding wild-type polynucleotide or a corresponding polynucleotide of a different allelic variation. In some aspects, the methods also or alternatively are capable of sequencing multiple different alleles or different biomarkers, e.g., genetic variations, at a single locus simultaneously.

In some aspects, where the template contains the first and second segments and the extended target polynucleotide contains portions complementary to the first and second segments, respectively, the determining all or a portion of the nucleotide sequence of the extended target polynucleotide is carried out using: (1) a sequencing primer hybridizable to the portion complementary to the first segment; (2) a sequencing primer hybridizable to the portion complementary to the second segment; or (3) a sequencing primer hybridizable to the portion complementary to the first segment and the portion complementary to the second segment.

In some aspects, the portion of the target sequence containing the biomarker (e.g., the genetic or epigenetic marker, allelic difference, gene sequence, point mutation, SNP, insertion, deletion, etc.) is in a portion of the target polynucleotide which does not include complementarity to the template polynucleotide. In such an aspect, the portion of the extended target polynucleotide containing the biomarker is not complementary to the template polynucleotide.

In some aspects, the determining step(s) is or are carried out by next-generation sequencing. In some examples, the next-generation sequencing determines at least thousands of nucleic acid sequences in an intrinsically parallel manner. In some aspects, the next-generation sequencing includes one or more of pyrosequencing, sequencing by ligation, sequencing by SOLiD™ technology, sequencing by synthesis using modified nucleotides, sequencing by TruSeq™, HiSeg™, HeliScope™, PacBio RS, sequencing by ion detection technologies, sequencing by Ion Torrent™ technology, sequencing using DNA nanoballs, or nanopore-based sequencing. In some aspects, the determining of sequence is carried out using a detectable probe, for example, a detectable probe containing a label or an antibody, a fluorescent probe, or a radiolabeled probe. In some aspects, the determining of sequence includes contacting the sample with a restriction enzyme, carrying out fragment analysis, and/or conducting mass spectrometry or nuclear magnetic resonance imaging. In some aspects, the determination of sequencing is carried out using a sequencing method described herein.

In some embodiments, the methods further include amplifying the extended target polynucleotide, for example, to generate sufficient copies for sequencing, such as amplification prior to sequencing. In some aspects, where the template contains the first and second segments and the extended target polynucleotide contains portions complementary to the first and second segments, respectively, the amplifying is carried out using a primer hybridizable to the portion complementary to the second segment. In some examples, the amplifying is carried out by a polymerase chain reaction (PCR). Thus, in some embodiments, the term extended target polynucleotide refers to a copy thereof generated by amplification.

In some embodiments, the sample is or is derived from a biological sample, such as a body fluid, for example, a blood, plasma, serum, tissue, saliva, serum, urine, or semen sample, such as a whole blood sample, blood cells, or blood plasma.

In some aspects, the methods detect the target polynucleotide and/or determine the biomarker in the sample at a concentration of as low as one copy per 10, 20, 30, 40, 50, or 100 mL of sample, such as low as one copy per 20 mL sample. In some aspects, the methods detect the target polynucleotide and/or determine or detect the biomarker at a frequency as low as one copy of target sequence per one million copies of a corresponding wild-type sequence or sequence not containing the biomarker.

In some embodiments, provided are sequencing methods, e.g., multiplexing sequencing methods, that allow for simultaneous sequencing of multiple (first, second, etc.) different polynucleotides by employing multiple (first, second, etc.) sequencing primers, where the second sequencing primer is designed to be larger in size and/or molecular weight than any of the products generated by extension using the first sequencing primer and chain-terminating nucleotides, where, for example, sanger sequencing is used to determine sequence. Thus, products generated by the first, second, third, etc., sequencing primers can be distinguished, e.g., separated based on size or molecular weight, allowing for simultaneous sequencing of multiple polynucleotides with a plurality of biomarkers. Such sequencing methods may be used in conjunction with the capturing and/or amplification methods provided herein, for detection of biomarkers, e.g., genetic variations, for example, at low copy numbers and/or based on products of extension of small DNA fragments from biological samples.

For example, in some embodiments, the target polynucleotide is a first target polynucleotide and the sample further comprises a second (and optionally third, fourth, fifth, and so-forth) target polynucleotide(s) with a second, and optionally third, fourth, fifth, and so-forth, biomarker. In some aspects, step (a) further includes contacting the sample with a second (and/or third, fourth, fifth, and so forth) template polynucleotide hybridizable to the second (and/or third, fourth, fifth, and so forth) target polynucleotide, under conditions whereby the second (and/or third, fourth, fifth, and so forth) target polynucleotide hybridizes to the second template polynucleotide. In some aspects, step (b) is carried out under conditions that permit extension of the second (and/or third, fourth, fifth, and so forth) target polynucleotide by the polymerase, thereby producing a second (and/or third, fourth, fifth, and so forth extended target polynucleotide). In some aspects, step (c) or a determining step further includes determining the nucleotide sequence of all or a portion of the second (and/or third, fourth, fifth, and so forth) extended target polynucleotide comprising the second (and/or third, fourth, fifth, and so forth) biomarker, thereby detecting the presence of the second (and/or third, fourth, fifth, and so forth) polynucleotide in the sample and determining the second (and/or third, fourth, fifth, and so forth) biomarker.

In some such embodiments, step (c) or the determining step is carried out by (i) combining in a reaction mixture the first and second (and/or third, fourth, fifth, and so forth)

extended target polynucleotides, first and second (and/or third, fourth, fifth, and so forth) labeled sequencing primers hybridizable respectively to the first and second (and/or third, fourth, fifth, and so forth) extended target polynucleotides, a polymerase, nucleotides, and a chain-terminating nucleotide, under conditions that permit hybridization of the first and second (and/or third, fourth, fifth, and so forth) sequencing primers to the first and second (and/or third, fourth, fifth, and so forth) extended target polynucleotides, respectively, and extension of the first and second (and/or third, fourth, fifth, and so forth) sequencing primers, wherein the periodic incorporation of the chain-terminating nucleotide by the polymerase terminates polymerization. In some aspects, such reaction thereby produces a pool of first target products of a plurality of lengths having complementarity to the first extended target polynucleotide and a pool of second target products of a plurality of lengths having complementarity to the second extended target polynucleotide (and optionally, a pool of third target products of a plurality of lengths having complementarity to the third extended target polynucleotide, and so-forth). In some aspects, the second sequencing primer has a molecular weight at least as large as or larger than the largest of the first target products, for example, such that each of the second target products has a molecular weight greater than each of the first target products. In some aspects, the second sequencing primer has a molecular weight at least as large as or larger than the first extended target polynucleotide (and optionally, the third sequencing primer has a molecular weight at least as large as or larger than the second extended target polynucleotide, and so forth). In some aspects, step (c) further includes (ii) differentiating the products based on differences of molecular weight. In some aspects, first target products are separated from the second target products (and optionally, so-forth) based on molecular weight.

In some embodiments, the provided sequencing methods allow for simultaneous sequencing and detection of a biomarker (e.g., genetic variation or mutation) in the presence of the corresponding sequence, such as a normal or wild-type sequence, for example, where the biomarker is present in relatively low copy number or concentration compared to the corresponding sequence. In some eases, the methods detect both the biomarker and the corresponding sequence (thus deemed another or second biomarker) simultaneously. In some aspects, the corresponding sequence contains only a single nucleotide difference compared to the biomarker, and/or is 99, 98, 97, 96, 95, 94, 93, 92, 91, 90, 85, or 85% identical to the biomarker.

In some aspects, the detection of the biomarker in the presence of the corresponding sequence or detection of both simultaneously, is achieved by using a plurality of different sequencing primers, each containing at its 3' terminus a nucleotide that pairs with or is complementary to the nucleotide present at the position of interest of the variant and wild-type or normal sequences, respectively. For example, if a particular genetic variation is characterized by a "T" at a certain position as compared with a "C" in the wild-type or normal sequence, two primers would be used that could be otherwise identical but contain an "A" and "G," at their 3' ends respectively, and thus at the nucleotide position that pairs with the corresponding or paired position when hybridized to the polynucleotide of interest. In this way, the first primer would only prime extension when paired to a polynucleotide containing the mutant or varied sequence, whereas the second primer would only prime extension when paired to a polynucleotide containing the wild-type or normal position. In some aspects, such primers are designed such that one primer is larger in size or molecular weight than all products generated by extension with the other primer, such that products of extension using the two primers can be separated from one another based on size or molecular weight. Thus, sequencing reaction is carried out and multiple different allelic variants of the same locus may be determined simultaneously. Such sequencing methods may be used in conjunction with the capturing and/or amplification methods provided herein, for detection of biomarkers, e.g., genetic variations, for example, at low copy numbers and/or based on products of extension of small DNA fragments from biological samples.

For example, in some embodiments, provided are methods carried out by (a) combining a first extension primer, a second extension primer, a polymerase, and a sample containing a first polynucleotide, a second polynucleotide, or both the first and second polynucleotides, under conditions whereby the first primer is extended by the polymerase when hybridized to the first polynucleotide, thereby producing a pool of first extension products and the second primer is extended by the polymerase when hybridized to the second polynucleotide, thereby producing a pool of second extension products; and (b) differentiating the extension products based on differences in molecular weight, for example, separating the first extension products from the second extension products based on molecular weight. In some aspects of the provided detection, assay, and determination methods, determination of sequence is carried out by a method of this embodiment. In some aspects, the first extension primer contains sequence identity to the second extension primer, for example, such that each of the first and second extension primers is hybridizable to each of the first and second polynucleotides. In some aspects, the 3'-terminal residue of the first extension primer is a first nucleotide, which is complementary to a paired nucleotide in the first polynucleotide when the first extension primer is hybridized to the first polynucleotide. In some aspects, the 3'-terminal residue of the second extension primer is a second nucleotide, which is complementary to a paired nucleotide in the second polynucleotide when the second extension primer is hybridized to the second polynucleotide. Typically, the second nucleotide is different from the first nucleotide, for example, is a different nucleobase or contains a modification not present in the first nucleotide. In some aspects, the second extension primer has a molecular weight that is greater than that of each of the first extension products. In some aspects, the second extension primer has a molecular weight that is greater than that of the first polynucleotide or at least 2 times greater than that of the first extension primer.

In some aspects, detection, identification, and/or determining the presence of the target sequence and/or target polynucleotide provides diagnostic and/or prognostic information about a disease, disease state, and/or condition, for example, in a subject from which the biological sample is taken. For example, in some aspects, the detection, determination, or identification of the target polynucleotide or biomarker in the sample determines the presence, absence severity, prognosis, stage, or other information about a disease, condition, or other event, such as cancer, tumor, metastasis, malignancy, proliferative disease or disorder, prenatal or fetal condition, genetic predisposition, hereditary disease or condition, genetic defect congenital disease or condition, genotype, autoimmune or inflammatory disease or condition, cardiovascular disease or condition, metabolic disease or condition, transplant acceptance or rejection, or likelihood of success or treatment outcome using a particular therapy or treatment, such as drug, biologic, surgery, device, transplantation, intervention, or other treatment, in or by the subject from which the biological sample is taken. In some examples, the condition is a healthy state.

Also provided are template polynucleotides, for example, for use in the provided methods, and compositions containing the same, such as the template polynucleotides described herein.

Also provided are sequencing primers for use in connection with the provided methods, and compositions containing the same. For example, in one embodiment, provided is a composition containing two or more sequencing primers, each complementary to two different corresponding biomarkers (e.g., those corresponding to a mutant and wild-type allele of a gene), and each, respectively, containing at its 3' terminus a nucleotide that pairs with, i.e., is complementary to, the nucleotide present at the corresponding position in the respective biomarkers.

For example, if a particular genetic variation is characterized by a "T" at a certain position as compared with a "C" in the wild-type or normal sequence, two primers could be used, for example that share identity, but that an "A" and "G," are present at their 3' ends respectively, and thus are present at the nucleotide position of the respective primer that pairs with the corresponding or paired position when hybridized to a polynucleotide containing the variant or wild-type position. In some examples, the primers are otherwise 100% identical, or at least 99, 98, 97, 96, 95, 94, 93, 92, 91, or 90% identical, except for this 3' terminal nucleotide.

In some aspects, the second extension primer in the composition has a molecular weight that is greater than that of each of the first extension products that could be generated by the first in a sequencing reaction. In some aspects, the second extension primer has a molecular weight that is greater than that of the first polynucleotide, and so forth, for multiple additional primers. In some aspects, the second extension primer has a molecular weight that is at least 1.5, 2, 3, 4, 5, or more times the molecular weight of the first extension primer. In some aspects, the second extension primer is at least 40, 45, 50, 55, 60, 65, 70, 75, 80, 85, 90, or 100 nucleotides in length.

In some aspects, the third extension primer has a molecular weight that is at least 1.5, 2, 3, 4, 5, or more times the molecular weight of the second extension primer; and the fourth extension primer has a molecular weight that is at least 1.5, 2, 3, 4, 5, or more times the molecular weight of the third extension primer. In some aspects, the third extension primer is at least 40, 45, 50, 55, typically at least 60, 65, 70, 75, 80, 85, 90, or 100 nucleotides in length. In some examples, the sequencing primers have the sequences set forth in any one or more of SEQ ID NOS:6 and 7.

Also provided are amplification primers for use in connection with the methods. In some examples, the amplification primers have the sequences set forth in any of SEQ ID NOS:4 and 5.

BRIEF DESCRIPTION OF THE DRAWINGS

FIG. 10A depicts alignment between a template polynucleotide (SEQ ID NO:1) and a synthetic target polynucleotide (SEQ ID NO:4). The bolded nucleotides are part of a codon encoding V600 in wild-type BRAF. FIG. 10B depicts alignment between a template polynucleotide (SEQ ID NO:8) and a synthetic target polynucleotide (SEQ ID NO:2). The bolded nucleotides are part of a codon encoding E600 in the V600E BRAF mutant. FIG. 10C depicts alignment between SEQ ID NO:8 and a synthetic target polynucleotide (SEQ ID NO:3). The bolded nucleotides are part of a codon encoding E600 in the V600E BRAF mutant.

DETAILED DESCRIPTION

Figure 1:
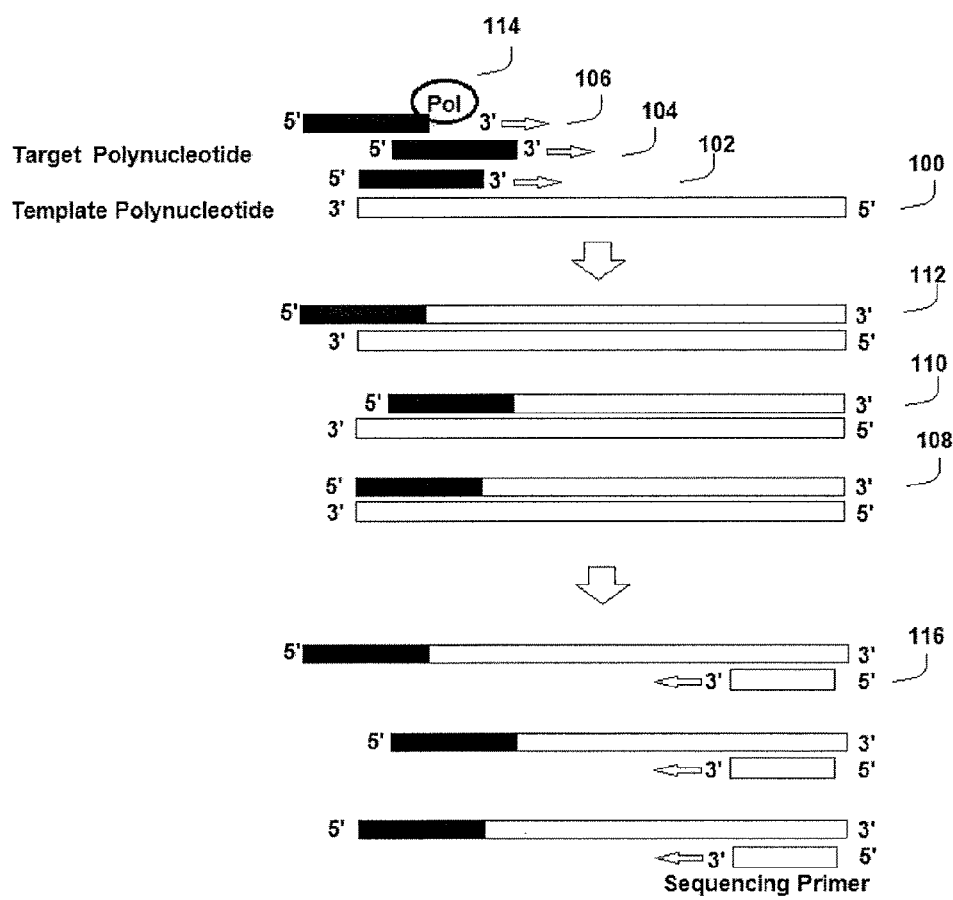
FIG. 1 depicts a method according to an example of the present disclosure. A target polynucleotide (which may include a plurality of target polynucleotides) having a biomarker is hybridized to a template polynucleotide, and is extended by a polymerase to produce an extended target polynucleotide. In this example, the nucleotide sequence of all or a portion of the extended target polynucleotide is then determined using a sequencing primer.

A detailed description of one or more embodiments of the claimed subject matter is provided along with accompanying figures that illustrate certain principles of the claimed subject matter. The claimed subject matter is described in connection with such embodiments, but is not limited to any embodiment. It is to be understood that the claimed subject matter may be embodied in various forms, and encompasses numerous alternatives, modifications and equivalents. Therefore, specific details disclosed herein are not to be interpreted as limiting. The claimed subject matter may be practiced according to the claims without some or all of these specific details. It is to be understood that other embodiments can be used and structural changes can be made without departing from the scope of the claimed subject matter. For the purpose of clarity, technical material that is known in the technical fields related to the claimed subject matter has not been described in detail so that the claimed subject matter is not unnecessarily obscured.

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

All publications, including patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The practice of the provided embodiments will employ, unless otherwise indicated, conventional techniques and descriptions of organic chemistry, polymer technology, molecular biology (including recombinant techniques), cell biology, biochemistry, and sequencing technology, which are within the skill of those who practice in the art. Specific illustrations of suitable techniques can be had by reference to the examples herein. Such conventional techniques include polynucleotide sequencing, hybridization and ligation of polynucleotides, and detection of hybridization. However, other equivalent techniques and procedures can also be used, including those found in standard laboratory manuals such as Green, et al., Eds., *Genome Analysis: A Laboratory Manual Series* (Vols. I-IV) (1999); Weiner, Gabriel, Stephens, Eds., *Genetic Variation: A Laboratory Manual* (2007); Dieffenbach, Dveksler, Eds., *PCR Primer: A Laboratory Manual* (2003); Bowtell and Sambrook, *DNA Microarrays: A Molecular Cloning Manual* (2003); Mount, *Bioinformatics: Sequence and Genome Analysis* (2004); Sambrook and Russell, *Condensed Protocols from Molecular Cloning: A Laboratory Manual* (2006); and Sambrook and Russell, *Molecular Cloning: A Laboratory Manual* (2002) (all from Cold Spring Harbor Laboratory Press); Ausubel, et al. eds., *Current Protocols in Molecular Biology* (1987); T. Brown ed., *Essential Molecular Biology* (1991), IRL Press; Goeddel ed., *Gene Expression Technology* (1991), Academic Press; A. Bothwell, et al., eds., *Methods for Cloning and Analysis of Eukaryotic Genes* (1990), Bartlett Publ.; M. Kriegler, *Gene Transfer and Expression* (1990), Stockton Press; R. Wu, et al., eds., *Recombinant DNA Methodology* (1989), Academic Press; M. McPherson, et al., *PCR: A Practical Approach* (1991), IRL Press at Oxford University Press; Stryer, *Biochemistry* (4th Ed.) (1995), W. H. Freeman, New York N.Y.; Gait, *Oligonucleotide Synthesis: A Practical Approach* (2002), IRL Press, London; Nelson and Cox, *Lehninger, Principles of Biochemistry* (2000) 3rd Ed., W. H. Freeman Pub., New York, N.Y.; and Berg, et al., *Biochemistry* (2002) 5th Ed., W. H. Freeman Pub., New York, N.Y., all of which are herein incorporated in their entirety by reference for all purposes.

Outline
1. Definitions
2. Methods and systems for detecting and assaying polynucleotides and genetic markers Available methods
   Methods for capturing, amplifying, and detecting polynucleotides and biomarkers
3. Samples
4. Biomarkers
5. Target polynucleotides
6. Template polynucleotides
7. Extension and ligation
   Extension using biomarker-containing target polynucleotides as primers
   Agents for extension and extension process
   Ligation using synthetic template
8. Amplification and processing
9. Identification, detection, and sequencing
   Multiplex sequencing
   Allele-specific sequencing
10. Sequencing polynucleotides
11. Applications and uses

1. DEFINITIONS

As used herein, the singular forms "a," "an," and "the" include plural referents unless the context clearly dictates otherwise. For example, "a" or "an" means "at least one" or "one or more." Thus, reference to "a template polynucleotide" can refer to one or more template polynucleotides, and reference to "the method" includes reference to equivalent steps and methods disclosed herein and/or known to those skilled in the art, and so forth.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

The term "about" as used herein refers to the usual error range for the respective value readily known to the skilled person in this technical field. Reference to "about" a value or parameter herein includes (and describes) embodiments that are directed to that value or parameter per se.

As used herein, an individual includes any living organism, such as humans and other mammals. A subject as used herein includes an organism to which the provided compositions, methods, or systems can be administered or applied. Mammals include, but are not limited to, humans, and non-human animals, including farm animals, sport animals, rodents and pets.

In certain aspects of the present disclosure, a biological sample or material can be obtained and used, and can refer to any sample or material obtained from a living or viral source or other source of macromolecules and biomolecules, and includes any cell type or tissue of a subject from which nucleic acid or protein or other macromolecule can be obtained. The biological sample can be a sample obtained directly from a biological source or a sample that is processed. For example, isolated nucleic acids that are amplified constitute a biological sample. Biological samples include, but are not limited to, body fluids, such as blood, plasma, serum, cerebrospinal fluid, synovial fluid, urine and sweat, tissue and organ samples from animals and plants and processed samples derived therefrom.

As used herein, a composition refers to any mixture of two or more products, substances, or compounds. It may be a solution, a suspension, liquid, powder, a paste, aqueous, non-aqueous or any combination thereof.

The terms "polynucleotide," "oligonucleotide," "nucleic acid" and "nucleic acid molecule" are used interchangeably herein to refer to a polymeric form of nucleotides of any length, and can include ribonucleotides (e.g., containing D-ribose), deoxyribonucleotides (e.g., containing 2-deoxy-D-ribose), analogs thereof, or mixtures thereof. The terms refer only to the primary structure of the molecule. Thus, the terms include triple-, double- and single-stranded deoxyribonucleic acid (DNA), as well as triple-, double- and single-stranded ribonucleic acid (RNA), including tRNA, rRNA, hRNA, mRNA (spliced or unspliced), any other type of polynucleotide which is an N- or C-glycoside of a purine or pyrimidine base, and other polymers containing non-nucleotidic backbones, for example, polyamide (e.g., peptide nucleic acids ("PNAs")) and polymorpholino (commercially available from, e.g., Anti-Virals, Inc., Corvallis, Oreg., as Neugene) polymers, and other synthetic sequence-specific nucleic acid polymers providing that the polymers contain nucleobases in a configuration which allows for base pairing and base stacking, such as is found in DNA and RNA. Thus, these terms include, for example, 3'-deoxy-2', 5'-DNA, oligodeoxyribonucleotide N3' to P5' phosphoramidates, 2'-O-alkyl-substituted RNA, hybrids between DNA and RNA or between PNAs and DNA or RNA, and also include known types of modifications, for example, labels, alkylation, "caps," substitution of one or more of the nucleotides with an analog, internucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalkylphosphoramidates, aminoalkylphosphotriesters), those containing pendant moieties, such as, for example, proteins (including enzymes (e.g. nucleases), toxins, antibodies, signal peptides, poly-L-lysine, etc.), those with intercalators (e.g., acridine, psoralen, etc.), those containing chelates (of, e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide. A nucleic acid generally will contain phosphodiester bonds, although in some cases nucleic acid analogs may be included that have alternative backbones such as phosphoramidite, phosphorodithioate, or methylphophoroamidite linkages; or peptide nucleic acid backbones and linkages. Other analog nucleic acids include those with bicyclic structures including locked nucleic acids, positive backbones, non-ionic backbones and non-ribose backbones. Modifications of the ribose-phosphate backbone may be done to increase the stability of the molecules; for example, PNA:DNA hybrids can exhibit higher stability in some environments. The terms "polynucleotide," "oligonucleotide," "nucleic acid" and "nucleic acid molecule" include any suitable length, such as at least 5, 6, 7, 8, 9, 10, 20, 30, 40, 50, 100, 200, 300, 400, 500, 1,000 or more nucleotides. Nucleic acids can also form stable complex with themselves or others, for example, DNA-protein complex, DNA-DNA complex, DNA-RNA complex.

It will be appreciated that, as used herein, the terms "nucleoside" and "nucleotide" will include those moieties which contain not only the known purine and pyrimidine bases, but also other heterocyclic bases which have been modified. Such modifications include methylated purines or pyrimidines, acylated purines or pyrimidines, or other heterocycles. Modified nucleosides or nucleotides can also include modifications on the sugar moiety, e.g., wherein one or more of the hydroxyl groups are replaced with halogen, aliphatic groups, or are functionalized as ethers, amines, or the like.

A primer, as used herein, e.g., an extension primer, a sequencing primer, or an amplification primer, refers to an oligonucleotide, either natural or synthetic, that is capable, upon forming a duplex with a template polynucleotide, of acting as a point of initiation of nucleic acid synthesis and being extended from its 3' end along the template so that an extended duplex is formed. The sequence of nucleotides added during the extension process is determined by the sequence of the template polynucleotide. Primers usually are extended by a polymerase, e.g., a DNA polymerase. In some embodiments, the target polynucleotides of the provided methods are primers.

An extension primer as used herein includes a polynucleotide sequence that is complementary to a template polynucleotide, and which is capable of hybridizing to and extending a sequence, for example under polymerase chain reaction conditions, to produce an extension product.

A template polynucleotide refers to a polynucleotide that contains a nucleic acid sequence that can bind to a corresponding primer, such as the target polynucleotide, and serve as a template for extension of the primer by a polymerase. The polynucleotide region of a template polynucleotide may be composed of DNA, RNA, and/or synthetic nucleotide analogs.

The terms "complementary" and "substantially complementary" refer to the ability to hybridize or base pair or form of a duplex between nucleotides or nucleic acids, for instance, between the two strands of a double-stranded DNA molecule or between an oligonucleotide primer and a primer binding site on a single-stranded nucleic acid. Complementary nucleotides are, generally, A and T (or A and U), or C and G. Two single-stranded polynucleotides, e.g., RNA or DNA, or regions thereof, are said to be complementary or substantially complementary when the nucleotides of one strand or region, optimally aligned and compared with at appropriate nucleotide insertions or deletions, pair with at least about 40%, at least about 50%, at least about 60%, at least about 70%, or at least about 80% of the other strand or region, usually at least about 90% to about 95%, and even about 98% to about 100%. Sequence identity or complementarity can be measured along the full length of a polynucleotide or along a region of the molecule. In one aspect, two complementary sequences of nucleotides are capable of hybridizing, for example, with less than 25%, for example, with less than 15%, for example, with less than 5%, for example, with no mismatches between opposed nucleotides. In some aspects, the two molecules will hybridize under conditions of high stringency.

Hybridization as used herein refers to the process in which two single-stranded polynucleotides bind non-covalently to form a stable double-stranded polynucleotide. In one aspect, the resulting double-stranded polynucleotide can be a hybrid or duplex. Hybridization conditions typically include salt concentrations of approximately less than 1 M, often less than about 500 mM and may be less than about 200 mM. A hybridization buffer includes a buffered salt solution such as 5% SSPE, or other such buffers known in the art. Hybridization temperatures can be as low as 5° C., but are typically greater than 22° C., and more typically greater than about 30° C., and typically in excess of 37° C. Hybridizations are often performed under stringent conditions, i.e., conditions under which a sequence will hybridize to its target sequence but will not hybridize to other, non-complementary sequences. Stringent conditions are sequence-dependent and are different in different circumstances. For example, longer fragments may require higher hybridization temperatures for specific hybridization than short fragments. As other factors may affect the stringency of hybridization, including base composition and length of the complementary strands, presence of organic solvents, and the extent of base mismatching, the combination of parameters is more important than the absolute measure of any one parameter alone. Generally stringent conditions are selected to be about 5° C. lower than the $T_m$ for the specific sequence at a defined ionic strength and pH. The melting temperature $T_m$ can be the temperature at which a population of double-stranded nucleic acid molecules becomes half dissociated into single strands. Several equations for calculating the $T_m$ of nucleic acids are well known in the art. As indicated by standard references, a simple estimate of the $T_m$ value may be calculated by the equation, $T_m=81.5+0.41$ (% G+C), when a nucleic acid is in aqueous solution at 1 M NaCl (see e.g., Anderson and Young, 1985, "Quantitative Filter Hybridization," in Nucleic Acid Hybridization). Other references (e.g., Allawi and SantaLucia, Jr., 1997, Biochemistry, 36:10581-94) include alternative methods of computation which take structural and environmental, as well as sequence characteristics into account for the calculation of $T_m$.

In general, the stability of a hybrid is a function of the ion concentration and temperature. Typically, a hybridization reaction is performed under conditions of lower stringency, followed by washes of varying, but higher, stringency. Exemplary stringent conditions include a salt concentration of at least 0.01 M to no more than 1 M sodium ion concentration (or other salt) at a pH of about 7.0 to about 8.3 and a temperature of at least 25° C. For example, conditions of 5×SSPE (750 mM NaCl, 50 mM sodium phosphate, 5 mM EDTA at pH 7.4) and a temperature of approximately 30° C. are suitable for allele-specific hybridizations, though a suitable temperature depends on the length and/or GC content of the region hybridized. In one aspect, stringency of hybridization in determining percentage mismatch can be as follows: 1) high stringency: 0.1×SSPE, 0.1% SDS, 65° C.; 2) medium stringency: 0.2×SSPE, 0.1% SDS, 50° C. (also referred to as moderate stringency); and 3) low stringency: 1.0×SSPE, 0.1% SDS, 50° C. It is understood that equivalent stringencies may be achieved using alternative buffers, salts and temperatures. For example, moderately stringent hybridization can refer to conditions that permit a nucleic acid molecule such as a probe to bind a complementary nucleic acid molecule. The hybridized nucleic acid molecules generally have at least 60% complementarity, including for example at least any of 70%, 75%, 80%, 85%, 90%, or 95% complementarity. In certain embodiments, moderately stringent conditions include conditions equivalent to hybridization in 50% formamide, 5×Denhardt's solution, 5×SSPE, 0.2% SDS at 42° C., followed by washing in 0.2×SSPE, 0.2% SDS, at 42° C.; high stringency conditions include conditions equivalent to by hybridization in 50% formamide, 5×Denhardt's solution, 5×SSPE, 0.2% SDS at 42° C., followed by washing in 0.1×SSPE, and 0.1% SDS at 65° C.; low stringency hybridization include conditions equivalent to hybridization in 10% formamide, 5×Denhardt's solution, 6×SSPE, 0.2% SDS at 22° C., followed by washing in 1×SSPE, 0.2% SDS, at 37° C. Denhardt's solution contains 1% Ficoll, 1% polyvinylpyrolidone, and 1% bovine serum albumin (BSA). 20×SSPE (sodium chloride, sodium phosphate, ethylene diamide tetraacetic acid (EDTA)) contains 3M sodium chloride, 0.2 M sodium phosphate, and 0.025 M EDTA. Other suitable moderate stringency and high stringency hybridization buffers and conditions are well known to those of skill in the art and are described, for example, in Sambrook, et al., Molecular Cloning: A Laboratory Manual, 2nd ed., Cold Spring Harbor Press, Plainview, N.Y. (1989); and Ausubel, et al., Short Protocols in Molecular Biology, 4th ed., John Wiley & Sons (1999).

Alternatively, substantial complementarity exists when an RNA or DNA strand will hybridize under selective hybridization conditions to its complement. Typically, selective hybridization will occur when there is at least about 65% complementary over a stretch of at least 14 to 25 nucleotides, for example, at least about 75%, for example, at least about 90% complementary. See M. Kanehisa, 1984, Nucleic Acids Res. 12:203.

While there exists a number of methods to measure identity or complementarity between two polynucleotides, the term "identity" is well known to skilled artisans (Carrillo, H. & Lipman, D., *SIAM J Applied Math* 48:1073 (1988)). Sequence identity or complementarity compared along the full length of two polynucleotides refers to the percentage of identical or complementary nucleotide residues along the full-length of the molecule. For example, if a polynucleotide A has 100 nucleotide and polynucleotide B has 95 nucleotides, which are identical to nucleotides 1-95 of polynucleotide A, then polynucleotide B has 95% identity when sequence identity is compared along the full length of a polynucleotide A compared to full length of polynucleotide B. Alternatively, sequence identity between polynucleotide A and polynucleotide B can be compared along a region, such as a 20 nucleotide analogous region, of each nucleotide. In this case, if polynucleotide A and B have 20 identical nucleotides along that region, the sequence identity for the regions would be 100%. Alternatively, sequence identity can be compared along the length of a molecule, compared to a region of another molecule. As discussed below, and known to those of skill in the art, various programs and methods for assessing identity are known to those of skill in the art. High levels of identity, such as 90% or 95% identity, readily can be determined without software.

Whether any two nucleic acid molecules have sequences that contain, or contain at least, a certain percent (e.g. 60%, 70%, 80%, 85%, 90%, 95%, 96%, 97%, 98% or 99%) sequence identity or complementarity can be determined using known computer algorithms such as the "FASTA" program, using for example, the default parameters as in Pearson, et al. (1988) *Proc. Natl. Acad. Sci. USA* 85:2444 (other programs include the GCG program package (Devereux, J., et al., *Nucleic Acids Research* 12(I):387 (1984)), BLASTN, FASTA (Altschul, S. F., et al., *J Molec Biol* 215:403 (1990); *Guide to Huge Computers*, Martin J. Bishop, ed., Academic Press, San Diego, 1994, and Carrillo, et al. (1988) *SIAM J Applied Math* 48:1073). For example, the BLAST function of the National Center for Biotechnology Information database can be used to determine identity. Other commercially or publicly available programs include DNAStar "MegAlign" program (Madison, Wis.) and the University of Wisconsin Genetics Computer Group (UWG) "Gap" program (Madison Wis.)). The extent of sequence identity (homology) and complementarity may be determined using any computer program and associated parameters, including those described herein, such as BLAST 2.2.2. or FASTA version 3.0t78, with the default parameters. It is understood that for the purposes of determining sequence identity among DNA and RNA sequences thymidine nucleotide is equivalent to (represents identity with) a uracil nucleotide. Percent identity further can be determined, for example, by comparing sequence information using a GAP computer program (e.g., Needleman, et al. (1970) *J. Mol. Biol.* 48:443, as revised by Smith and Waterman ((1981) *Adv. Appl. Math.* 2:482). Briefly, the GAP program defines similarity as the number of aligned symbols (i.e., nucleotides or amino acids), which are similar, divided by the total number of symbols in the shorter of the two sequences. Default parameters for the GAP program can include: (1) a unary comparison matrix (containing a value of 1 for identities and 0 for non-identities) and the weighted comparison matrix of Gribskov, et al. (1986) *Nucl. Acids Res.* 14:6745, as described by Schwartz and Dayhoff, eds., *Atlas of Protein Sequence and Structure*, National Biomedical Research Foundation, pp. 353-358 (1979); (2) a penalty of 3.0 for each gap and an additional 0.10 penalty for each symbol in each gap; and (3) no penalty for end gaps.

Ligation refers to the formation of a covalent bond or linkage between the termini of two or more nucleic acids, e.g., oligonucleotides and/or polynucleotides. In certain aspects, ligation is carried out in a template-driven reaction. The nature of the bond or linkage may vary widely and the ligation may be carried out enzymatically or chemically. As used herein, ligations are usually carried out enzymatically to form a phosphodiester linkage between a 5'-terminal nucleotide of one oligonucleotide with a 3'-terminus of another oligonucleotide.

Sequence determination means determination of information relating to the nucleotide base sequence of a nucleic acid. Such information may include the identification or determination of partial as well as full sequence information of the nucleic acid. Sequence information may be determined with varying degrees of statistical reliability or confidence. In one aspect, the term includes the determination of the identity and ordering of a plurality of contiguous nucleotides in a nucleic acid. High throughput digital sequencing or next-generation sequencing means sequence determination using methods that determine many (typically thousands to billions) nucleic acid sequences in an intrinsically parallel manner, e.g., where DNA templates are prepared for sequencing not one at a time, but in a bulk process, and where many sequences are read out, e.g., in parallel, or alternatively using an ultra-high throughput serial process that itself may be parallelized. Such methods include but are not limited to pyrosequencing (for example, as commercialized by 454 Life Sciences, Inc., Branford, Conn.); sequencing by ligation (for example, as commercialized in the SOLiD™ technology, Life Technologies, Inc., Carlsbad, Calif.); sequencing by synthesis using modified nucleotides (such as commercialized in TruSeq™ and HiSeg™ technology by Illumina, Inc., San Diego, Calif.; HeliScope™ by Helicos Biosciences Corporation, Cambridge, Mass.; and PacBio RS by Pacific Biosciences of California, Inc., Menlo Park, Calif.), sequencing by ion detection technologies (e.g., Ion Torrent™ technology, Life Technologies, Carlsbad, Calif.); sequencing of DNA nanoballs (Complete Genomics, Inc., Mountain View, Calif.); nanopore-based sequencing technologies (for example, as developed by Oxford Nanopore Technologies, LTD, Oxford, UK), and like highly parallelized sequencing methods.

SNP (single nucleotide polymorphism) refers to a genetic variation between individuals, e.g., a single nitrogenous base position in the DNA of organisms that is variable. SNPs are found across the genome. Much of the genetic variation between individuals is due to variation at SNP loci, and this genetic variation can result in phenotypic variation between individuals. SNPs for use in the present disclosure and their respective alleles may be derived from any number of sources, such as public databases (U.C. Santa Cruz Human Genome Browser Gateway (genome.ucsc.edu/cgi-bin/hgGateway) or the NCBI dbSNP website (ncbi.nlm.nih gov/SNP/), or may be experimentally determined as described in U.S. Pat. No. 6,969,589 and U.S. Patent Application Publication No. US2006/0188875. Although the use of SNPs is described in some of the embodiments presented herein, it will be understood that other biallelic or multi-allelic genetic variations may also be used or detected by a method of the present disclosure. A biallelic genetic variation is one that has two polymorphic forms, or alleles. As mentioned above, for a biallelic genetic variation that is associated with a trait, the allele that is more abundant in the genetic composition of a case group as compared to a control group is termed the "associated allele," and the other allele can be referred to as the "unassociated allele." Thus, for each biallelic polymorphism that is associated with a given trait (e.g., a disease or drug response), there is a corresponding associated allele. Other biallelic polymorphisms that may be used or detected by the methods presented herein include, but are not limited to, multinucleotide changes, insertions, deletions, repeats, translocations, and epigenetic changes such as gene hypermethylation. The polymorphic loci that are screened in an association study may be in a diploid or a haploid state and, ideally, would be from sites across the genome.

It will be further appreciated that genetic or genomic variations include those in genomic DNA, mitochondrial DNA, episomal DNA, and/or derivatives of DNA such as amplicons, RNA transcripts, eDNA, DNA analogs, etc. Genetic or genomic changes that can be detected by a method of the present disclosure can be any types of DNA alterations including base change, deletion, duplication, amplification, polymorphism, microsatellite instability, loss of heterozygosity (LOH), epigenetic modification, and any combination thereof.

As used herein, biomarkers includes genetic and epigenetic markers, including, but not limited to mutations, SNPs, insertions, allelic differences, alleles, including mutant and wild-type alleles, genes or portions thereof, deletions, methylation, and demethylation. In some aspects, the biomarker is a wild-type allele, sequence, or residue. A sequence corresponding to the biomarker refers to a sequence containing complementarity to the biomarker or sequence containing the biomarker but not necessarily containing the biomarker itself, for example, a corresponding wild-type gene where the biomarker is a mutation or mutant form of a gene.

2. METHODS AND SYSTEMS FOR DETECTING AND ASSAYING POLYNUCLEOTIDES AND GENETIC MARKERS

Provided are methods and systems for capturing, amplifying, and/or detecting biomarkers, e.g., genetic and epigenetic markers such as variations, mutations, insertions, and deletions, such as those associated with one or more diseases, disease states, prognosis, stage, and/or conditions. In some aspects, the methods are useful in prognosis, diagnosis, staging, genetic testing, prenatal testing, and/or personalized medicine. Among the provided methods and systems are those that address various challenges and shortcomings of available methods.

Available Methods

Available detection methods include those carried out using Formalin-Fixed Paraffin Embedded (FFPE) samples and those that identify circulating cells, such as circulating tumor cells (CTCs). Detection and diagnostic methods often use various biological samples, such as blood, e.g., whole blood, blood plasma, and fractions or cells thereof, and tissue samples, such as formalin-fixed, paraffin-embedded tissue samples.

Available methods for detecting biomarkers are limited, for example, in terms of the amount or type of sample required and sensitivity. For example, certain methods require high sample amounts and/or are unable to detect biomarkers, e.g., genetic variations, below a certain copy number or with high background, such as below a certain ratio of cells carrying the biomarker to those not carrying it, e.g., wild-type or normal cells. Cellular and genetic heterogeneity, such as among different cancer cells (e.g., clonal variations), can limit detection and assaying in certain methods. For example, in certain cases of cancer diagnosis, biopsy samples undergo cellular enrichment using cancer-specific stains, in order to increase the ratio of cancer cells to wild-type cells. The enrichment process can account for up to about 40% of testing cost. Moreover, the cellular enrichment process can mean the failure to identify genetic markers, e.g., certain cancer cells and/or clonal cells, that do not react positively to the enrichment stains. Additionally, features of the enrichment process may interfere with downstream detection assays, such as PCR. For example, exposure to and/or removal of staining reagents can interfere with polymerases and other enzymes used in detection.

In the context of BRAF mutations, certain available methods detect a T1799A (V600E) mutation qualitatively in formalin-fixed, paraffin-embedded (FFPE) tissues, fresh/frozen tissue, peripheral blood, or bone marrow. In some such tests, BRAF mutations other than V600E and V600K are not detected. Such methods can achieve analytic sensitivity around 5% (i.e., 5 cancer cells per 95 wild-type cells). Available methods generally are based on amplification by PCR, followed by detection of the amplified nucleic acid segments by mutation-specific labeled DNA oligonucleotides. Clinical specimens, however, can contain substances that inhibit PCR amplification, such as heparin, hemoglobin, IgG or certain medications.

Sanger Sequencing, which has been the method of choice in detecting mutations in cancer tissues, has a sensitivity of less than 5%. Other methods such as Scorpions™ (Sigma-Aldrich) and COBAS® (e.g., COBAS® 4800 BRAF V600 Mutation Test, Roche) may have sensitivity of 1%-5%. Many such methods use non-verifiable, e.g., labeled probe, formats. In certain available sequencing methods, signal from the wild-type allele can suppress detection of the mutant allele, which thus may not be distinguishable from noise. For example, suppression of the mutant signal by the wild-type signal in Sanger sequencing alone can make the mutant signal indistinguishable from background noise signal and thus presents challenges in the context of detecting somatic mutation. Such limitations can lead to a compromised testing procedure that may not reflect the true picture which can be important for a desired treatment outcome.

In particular, challenges in detecting nucleic acids and biomarkers in bodily fluids include the inability of certain methods to (a) detect all or a plurality of biomarkers associated with a particular disease or condition (such as six mutations associated with colon cancer); and (b) detect those markers at sub-clinical concentrations (for example, in the context of pre-malignancy or sub-clinical nodal metastasis).

Provided herein are methods and systems that address such challenges.

Methods for Capturing, Amplifying, and Detecting Polynucleotides and Biomarkers

Provided are methods and systems for capturing, optionally amplifying, and detecting, e.g., sequencing, polynucleotides containing biomarkers, including genetic and epigenetic markers, e.g., SNPs, allelic variants, alleles, genes, insertions, deletions, and modifications. Among the methods are those having low limits of detection (LOD), e.g., with the ability to detect biomarkers at low or very low copy numbers, at sub-clinical concentrations, and and/or in the presence of polynucleotides or cells not containing the biomarkers (e.g., the detection of a mutant biomarker in the presence of wild-type polynucleotides or polynucleotides from normal cells).

In some aspects, the methods are particularly useful in detecting biomarkers contained within fragmented polynucleotides. In animals such as mammals, e.g., humans, the body continuously sheds intact cells, most of which are disintegrated, spilling various cellular components including bits and pieces of genetic materials (e.g., DNA and RNA) into the extracellular space. For example, fragmented nucleic acids can be found in the skin and body fluids, such as blood, urine and stool. In particular, millions of cells and debris from dead cells are shed daily into the blood, some of which remain as intact cells and eventually break down. For example, small but detectable amounts of DNA circulate in the blood of healthy people (Fedorov, et al., 1986, *Bull Exp. Biol. Med.* 102:1190-1192; Leon, et al., 1977, *Cancer Res.* 37:646-650) and other animals, and this amount has been found to increase in cancer states (Shapiro, et al., 1983, *Cancer* 51:2116-2120; Stroun, et al., 1989, *Oncology* 46:318-322). Although most of the cellular contents that are spilled into various body fluids are from normal cells, they can come from cells carrying genetic variations or markers, such as abnormal cells (e.g., cancer tissues), or cells carrying markers of genetic predisposition for various diseases (e.g., cystic fibrosis). Thus, blood can contain bits and pieces (fragments) of polynucleotides such as DNA, many having less than 1000 or less than 200 bases or base pairs in length, including those (e.g., fragmented DNA) shed from intact cells within bodily fluids or other extracellular samples, such as blood, urine, or stool, which often are present as small-sized fragments and at relatively low concentrations. Most DNA in bodily fluids exists as short, single-stranded DNA.

Although DNA is relatively stable, extracellular DNA often is broken and found in smaller pieces of various sizes and at low concentrations. Some of these disintegrated DNA fragments may carry vital information regarding a disease or condition (e.g., cancer mutations). Identification of such fragmented polynucleotides can provide valuable clinical information for early diagnosis, prevention, and management of disease. Provided are methods that capture, detect, and analyze biomarkers present in such fragments.

Thus, in some aspects, the provided methods are for the detection of bits and pieces (fragments) of polynucleotides at very low concentrations, carrying biomarkers, such as disease- or condition-specific markers (e.g., mutations), simultaneously in the presence of DNA from normal cells at subclinical concentrations from various samples, including bodily fluids.

In some embodiments, the methods address the challenge of the relatively small size of certain fragmented polynucleotides, such as those found in biological samples including bodily fluids. Due in part to their size and infrequency, such fragments can be difficult to identify and assess via conventional methods such as PCR and conventional sequencing approaches. In one aspect of the provided methods, these challenges are addressed by using such small fragments (deemed "target polynucleotides") as primers in extension reactions. Thus, in some aspects, the provided methods are distinct from available methods in that they employ fragmented polynucleotides present in biological samples and containing or suspected of containing biomarkers as the primers, rather than templates, in an extension reaction.

In such extension reactions, a template polynucleotide with a known sequence (e.g., a synthetic template) is combined with or provided to a biological sample or sample derived therefrom, for example, from a subject having or suspected of having a disease or condition or about which diagnostic or prognostic or personalized medicine information is to be determined. The template is typically synthetic and can be single- or double-stranded. In some aspects, it contains two regions: one (typically a 3' portion) having complementarity to the target in the portion(s) containing the biomarker(s) of interest, and another (typically a 5' portion) not having complementarity to the target, gene or locus of interest, and/or to the biomarker(s), such that it will not hybridize with the target. The 3' region is generally blocked or designed in a way that prohibits extension of the template polynucleotide by a polymerase.

The template is typically provided under conditions to allow hybridization to the target polynucleotide primer, and serves as a basis for extension of the target polynucleotide fragment containing the biomarker or variation of interest. In the case of multiple target polynucleotides, depending on the nucleotide makeup of the individual target polynucleotides, they can anneal at different sites along the length of the template. See the example shown in FIG. 1, where a template polynucleotide 100 containing the genomic region of interest is provided to a sample containing a plurality of short single-stranded DNA target polynucleotides 102, 104, and 106, under conditions where the target polynucleotide(s) hybridize to the template polynucleotide. A polymerase 114 extends the target polynucleotide. In some aspects, the process continues in a repeated mode by asymmetric amplification, for example, whereby additional target polynucleotide fragments or synthetic oligonucleotides serve as primers, or bidirectionally, for example, using a primer complementary to the portion of the extended target polynucleotide containing the target polynucleotide and another primer complementary to the portion containing complementarity to the template but not the target polynucleotide (see, e.g., FIGS. 4 and 6).

Alternatively, target polynucleotides are ligated based on the provided template polynucleotide, for example, using template-driven ligation. See FIG. 7. The product of such an extension or ligation is deemed an "extended target polynucleotide." See 108, 110, or 112 in FIG. 1.

In some embodiments, the extended target polynucleotide is optionally amplified, e.g., to generate sufficient copies of the biomarker for sequence determination, and all or part of its sequence (or the sequence of a copy thereof) determined, for example, via a sequencing reaction, to ultimately detect the biomarker in the target polynucleotide, in the sample, and for example, in a subject or biological sample from which the sample is derived. See for example, FIG. 1, in which a sequencing primer 116, hybridizable to the 3' end of the extended target polynucleotide, is used to sequence all or a portion of the extended target polynucleotide. Accordingly, sequence determination provides information about the target sequence, such as identifying the presence of or determining the sequence of all or part of the target polynucleotide, such as the biomarker. The biomarker may be detected qualitatively or quantitatively. In some aspects, the detection is quantitative, for example, using well-known methods such as real-time PCR (RT-PCR) or Q-PCR.

In some embodiments, although various target polynucleotides within the sample may contain complementarity to and hybridize to the template at different regions (see FIGS. 1 and 3), each of the extended target polynucleotides will contain sequence corresponding to the junction between the first and second (3' and 5') regions of the template polynucleotides, such that in sequencing reactions using sequencing primers, there is not any staggering of the nucleotide sequences generated. See FIG. 3.

Also provided are sequencing methods, for use alone or in combination with the provided extension or ligation methods. The provided sequencing include a multiplex (or multi loci) sequencing method and an allele-specific multiplex sequencing (ASMS) method, one or both of which in some embodiments is used to determining the nucleotide sequence of all or a portion of the extended target polynucleotide. Among the provided sequencing methods are those capable of sequencing multiple different polynucleotides simultaneously, sequencing and detecting polynucleotides with biomarkers, e.g., genetic variations, at very low copy number, for example, as low as at or about 1 copy of the biomarker or target polynucleotide in or per 1,000, 10,000, 100,000, or 1,000,000 total number of polynucleotides, or total number of corresponding polynucleotides, for example, in the case of a mutant biomarker, total number corresponding number of corresponding wild-type polynucleotides, in the sample or biological sample from which the sample is derived. Corresponding polynucleotides in some aspects are those that contain identity or complementarity to the gene, region, or locus of interest (e.g., in the gene, region, or locus, in which the biomarker is found); in some aspects, the corresponding polynucleotides do not contain the biomarker of interest, such as in the case of a mutant or variant biomarker, a corresponding wild-type polynucleotide or a corresponding polynucleotide of a different allelic variation. In some aspects, the methods also or alternatively are capable of sequencing multiple different alleles or different biomarkers, e.g., genetic variations, at a single locus simultaneously.

In some embodiments, multiple (first, second, etc.) different polynucleotides are sequenced by employing multiple (first, second, etc.) sequencing primers, where a second sequencing primer is designed to be larger in size and/or molecular weight than any of the products generated by extension using the first sequencing primer and chain-terminating nucleotides, where, for example, ranger sequencing is used to determine sequence. In one aspect, products generated by the different sequencing primers thus are distinguished, e.g., separated, based on size, allowing for simultaneous sequencing of multiple polynucleotides with a plurality of biomarkers. In some embodiments, the ASMS methods are modifications of the Sanger sequencing technology, in which one or more biomarker is sequenced and detected simultaneously with a corresponding sequence not containing the biomarker, e.g., where the biomarker that is a mutant or mutation, in the context of a normal or wild-type sequence, for example, where both sequences are present in the same reaction. For example, in some aspects, the methods use a plurality of different sequencing primers (e.g., first, second, etc. sequencing primers), each containing at its 3' terminus a nucleotide that pairs with, i.e., is complementary to, the nucleotide present at the corresponding position in either the variant sequence or the normal sequence when hybridized to a polynucleotide containing the variant or wild-type sequence. For example, if a particular genetic variation is characterized by a "T" at a certain position as compared with a "C" in the wild-type or normal sequence, two primers could be used, for example, that are otherwise identical except for the presence of an "A" and "G," respectively, at the nucleotide position that pairs with the corresponding or paired position when hybridized to a polynucleotide containing the variant or wild-type position. By virtue of this difference, in some aspects, the first primer primes extension only when paired to a polynucleotide containing the mutant or varied sequence, whereas the second primer primes extension only when paired to a polynucleotide containing the wild-type or normal position. In some aspects, the primers are designed such that one primer is larger in size or molecular weight than all products generated by extension with the other primer, such that products of extension using the two primers can be separated from one another based on size. Thus, sequencing reaction is carried out and multiple different allelic variants of the same locus may be determined simultaneously.

In some embodiments, the provided capture, amplification, detection, and sequencing methods address various challenges observed with available methods. For example, in some aspects, the methods capture, amplify, and/or detect of small polynucleotide fragments, e.g., fragments of less than 100, less than 200 or less than 100 nucleotides in length, such as those which are not amenable to PCR and sequencing by certain available methods, for example, by using such fragments as primers for extension based on synthetic templates. In some aspects, the methods are relatively non-invasive and/or inexpensive compared to other available methods. In some aspects, the methods readily use patient samples, such as blood or urine, or samples derived therefrom.

Among the methods provided herein are those that address certain challenges in detecting and sequencing nucleic acids from body fluids. For example, provided are methods capable of (a) detecting all or a plurality of mutations, markers, or other genetic variations associated with a particular disease or condition (e.g., six mutations associated with colon cancer), and/or (b) detecting such mutations at sub-clinical concentrations (for example, in the context of pre-malignancy or subclinical nodal metastases), for example, by providing a very low limit of detection (LOD). In certain aspects, the provided methods can distinguish between polynucleotides containing the biomarker, mutation, and/or variation of interest and those that do not contain it (such as wild-type polynucleotides or polynucleotides from normal cells) that also are present in the bodily fluid or other sample.

In some aspects, the ability to detect and determine sequence of such fragmented polynucleotides can provide important information regarding a disease or condition of interest, such as information regarding disease state, e.g., whether particular cancer-associated mutations are present. Hence, in some aspects, the provided methods are useful for identification of fragmented polynucleotides, e.g., DNA, for use in diagnosis, e.g., early diagnosis, prevention, and management of diseases and conditions.

In some aspects, the provided methods include: (1) isolating DNA or other polynucleotides from bodily fluids, which can be carried out using known methods, such as magnetic beads, membrane filtration, solid-phase separation, e.g., using sephadex columns (2) providing synthetic template and reagents for extension and/or amplification, such as PCR buffers, polymerase, nucleotides, thermocycling conditions, (3) purifying amplification products, e.g., using AMPure® beads, and (4) sequencing, such as by cycle sequencing, e.g., using any of the provided sequencing methods, for example, using primers having complementarity to the target, the synthetic template (e.g., the region not sharing complementarity with the gene or locus containing the biomarker of interest), or both.

3. SAMPLES

The provided methods generally are carried out using samples, typically biological samples and samples derived therefrom, containing the target polynucleotides. In some embodiments, the sample is obtained or derived from a subject having or suspected of having a particular disease or condition of interest. In some examples, the sample is or is derived from a bodily fluid, such as blood (e.g., whole blood or fraction thereof, such as plasma or serum), e.g., maternal blood, saliva, urine, spinal fluid, synovial fluid, amniotic fluid, lachrymal fluid, ichor, lymphatic fluid, or cerebrospinal fluid. In certain aspects, the sample is a liquid sample. In some aspects, the sample is extracellular fluid containing fragmented polynucleotides. In some aspects, the sample is an extracellular sample, for example, a sample that contains or is derived from an extracellular fluid, such as plasma. In some aspects, the sample contains other polynucleotides of interest, such as pathogen nucleic acids, e.g., viral or bacterial nucleic acids. In such examples, a viral or pathogenic nucleic acid may or may not be integrated into the genome of a cell of the subject from which the biological sample is obtained. Samples for use with the provided methods include those that are derived from such biological samples, such as those prepared as a result of nucleic acid purification from such a biological sample.

4. BIOMARKERS

The provided methods generally involve the identification or detection of the presence or absence of one or more biomarkers in the sample and/or subject from which the sample is obtained. Thus, in some embodiments, the sample, and more specifically the target polynucleotide(s) contained in the sample, contains one or more biomarker, such as a genetic or epigenetic marker, e.g., mutations, SNPs, insertions, allelic differences, alleles, including mutant and wild-type alleles, genes or portions thereof, deletions, methylation, and demethylation. In some aspects, the biomarker is a mutant or infrequently represented sequence, allele, or nucleotide; in other aspects, it is a wild-type or dominant sequence, allele, or nucleotide.

The fact that the sample or the target contains the biomarker is not to say that this information is known at the outset of the methods. In fact, the presence or absence of a biomarker in the sample or the target polynucleotide generally is unknown at the outset of the methods and this information is determined by the methods.

In some aspects, use of target polynucleotides (fragments) from a sample in which the presence of a biomarker of interest is unknown as a primer is a feature that distinguishes the provided methods from other identification methods.

The biomarker can include an epigenetic or genetic marker, such as a sequence including one or more genetic variations and/or genetic/epigenetic changes in genomic DNA, mtDNA, episomal DNA, RNA transcripts, tRNA, ncRNA, rRNA, hRNA, and/or derivatives of DNA such as amplicons, cDNA, DNA analogs, etc.

In certain embodiments, the biomarker is or includes all or part of a genetic locus having one or more genetic variations between individuals, e.g., one or more SNPs, where the presence of one or more such genetic variations is or are the biomarkers. In certain embodiments, the biomarker can include one or more biallelic or multi-allelic genetic variations. In the case of a biallelic genetic variation, the biomarker can relate to the associated allele or the unassociated allele. For example, the associated allele of a biallelic genetic variation is more abundant in the genetic composition of a case group as compared to a control group, therefore detection of the associated allele (e.g., with no or less unassociated allele detected) in a sample from a subject can be indicative of the associated trait in the subject. In some aspects, the biomarker includes one or more biallelic polymorphisms or genetic/epigenetic changes, including single or multi-nucleotide changes, based modifications, translocations, insertions, deletions, duplication, amplification, repeats, microsatellite instability, loss of heterozygosity, epigenetic modification, and any combinations thereof.

Exemplary base modifications include, but are not limited to methylation, uracil substitution, antibody conjugation, substitution with synthetic base, or substitution with synthetic sugar.

While the sequences of many genes are known, in many instances, the sequences and quantities of smaller extracellular gene fragments in the blood are not. The biomarker(s) being detected may be within a particular gene, genomic region, or locus of interest, for example, a gene associated with a particular disease state. In this case, a template polynucleotide containing the genomic region or locus can be provided.

In some embodiments, the biomarkers are or include cancer-associated mutations of oncogenes or tumor suppressor genes, including point mutation, insertions, deletions, and translocations, such as those contained in broken pieces of polynucleotides (e.g., DNA or RNA), for example, as shed from disintegrated cells, e.g., abnormal cells including cancer cells, such as those shed into the bloodstream. In some aspects, the biomarkers include all or part of the BRAF gene and/or BRAF mutations or alleles, for example, for analysis in the blood. Detection of the BRAF mutations in the extracellular BRAF fragments can be used as an indicator of human cancer.

Figure 3:
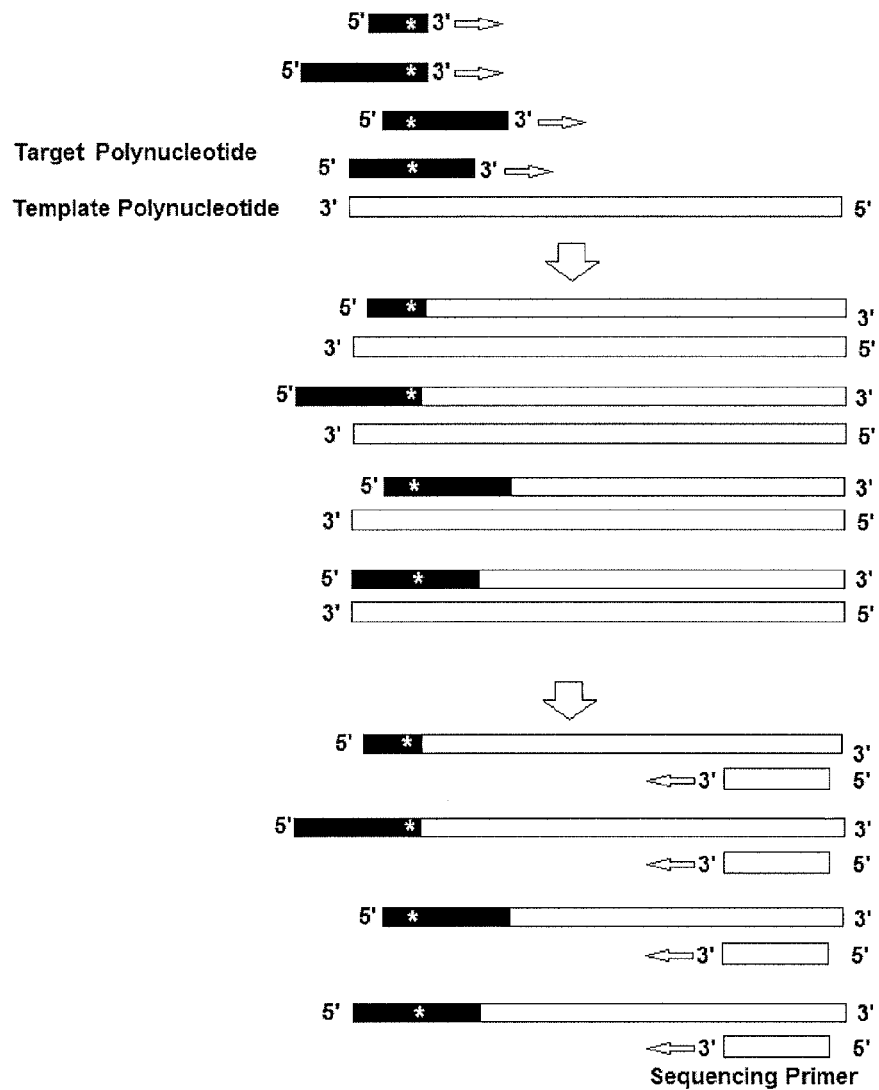
FIG. 3 depicts an example of a method according to an example of the present disclosure. The plurality of target polynucleotides shown contain the same mutation or single nucleotide mismatch compared to a template, indicated by the asterisk. The nucleotide sequence of the extended target polynucleotide for each target polynucleotide can be determined, e.g., by sequencing, which can provide information about the biomarker, for example, whether the mutation or single nucleotide mismatch is present.

In some embodiments, the target polynucleotide includes a plurality of target polynucleotides, each containing the genetic variation of interest and/or each containing the biomarker of interest. Such an embodiment is illustrated in FIG. 3, in which the asterisk represents a biomarker, e.g., genetic variation. In other aspects, the biomarker is an insertion or deletion or other modification. Thus, in certain aspects, the target polynucleotide includes a plurality of target polynucleotides, each comprising the biomarker. For example as shown in FIG. 3, in some embodiments, each of the plurality of target polynucleotides includes the same point mutation indicated by the asterisk.

The point mutation, for example, can be the V600E or V600D mutations of BRAF. After annealing to the template polynucleotide, each of the target polynucleotide is extended by a polymerase, producing an extended target polynucleotide containing the same point mutation. In certain embodiments, following determination of the nucleotide sequence of the extended target polynucleotides, each of the target polynucleotide sequence can be determined, including the same point mutation. The target polynucleotide sequence can be aligned and compared in order to identify the common point mutation. Thus, in one embodiment, a method of the present disclosure can be used to analyze a plurality of target sequences each comprising a target sequence of interest in a sample, thereby determining the concentration or frequency of the target sequence of interest in the sample or the biological sample from which the sample is obtained or derived.

In some embodiments, the methods are used to probe a plurality of biomarkers, e.g., simultaneously. Such a plurality can include, for example, two or more mutations, deletions, insertions, rearrangements, polymorphisms, SNPs, copy number variations, biallelic polymorphisms, multi-nucleotide changes, repeats, translocations, and/or epigenetic changes such as hypermethylations. In such embodiments, the sample may contain a first and second (and optionally third, and so forth) target polynucleotide, each containing a distinct biomarker. Each of the first, second, and so forth target polynucleotides can in some embodiments, themselves include multiple polynucleotides, e.g., a plurality of first target polynucleotides, each containing the first biomarker, a plurality of second target polynucleotides, each containing the second biomarker, and so forth.

In some aspects, one or more of the target polynucleotide contains the first and second (and so forth) biomarker. In general, in embodiments in which a plurality of biomarkers are assessed or detected, e.g., where a first, second, and so-forth target polynucleotide are present, corresponding first, second, and so forth template polynucleotides are used in connection with the provided methods.

Thus, in some aspects, a plurality of polynucleotide fragments carrying the same biomarker belong to a single species. In certain aspects, a single species can include uniform copies of target polynucleotides, which are of the same length and the same starting and ending nucleotide positions, all containing the biomarker of interest. In other aspects, target polynucleotides of a single species include varying copies, i.e., those of different lengths, and/or of different starting and/or ending nucleotide positions, each containing the biomarker of interest.

In another aspect, the target polynucleotide may include a plurality of polynucleotide fragments, which include a plurality of biomarkers, e.g., genetic changes or variations at different positions within a locus of interest, or with multiple different loci. In certain aspects, multiple species of target polynucleotides can include uniform copies of target polynucleotides, which are of the same length and the same starting and ending nucleotide positions. In other aspects, multiple species of target polynucleotides include varying copies, i.e., those of different lengths, and/or of different starting and/or ending nucleotide positions.

5. TARGET POLYNUCLEOTIDES

A target polynucleotide refers to one or more polynucleotides detected or assayed by the present methods. The target polynucleotide (or at least one of the target polynucleotides) generally contains a biomarker, though is generally unknown at the outset whether the target polynucleotide or the sample contains the biomarker. For example, it often is known or suspected that a particular sample, subject, or target polynucleotide has a particular gene or gene product of interest or portion thereof, but it is not known which form of the gene or product or portion thereof is present, such as whether the wild-type or mutant form is present, or which of several allelic variants are present, or whether the gene or gene product is present in its modified or unmodified form. Thus, the methods in many cases determine which form of a particular gene or portion or locus is present. The biomarker in some cases may be a wild-type nucleotide, sequence, or allele.

The target polynucleotide can be a polynucleotide of any suitable length, and can include ribonucleotides, deoxyribonucleotides, analogs thereof, or any combinations thereof. A target polynucleotide is typically naturally occurring, such as one or more DNA fragments in a bodily fluid such as an extracellular, e.g., blood, sample. A target polynucleotide in other aspects is synthetic. Target polynucleotides can be single-, double-, and/or triple-stranded DNA or RNA. Exemplary target polynucleotides include but are not limited to genomic DNA of various conformations (e.g., A-DNA, B-DNA, Z-DNA), mitochondria DNA (mtDNA), mRNA, tRNA, ncRNA, rRNA, hRNA, miRNA, and piRNA.

In some embodiments, the target polynucleotides are fragments. In some embodiments, the target polynucleotide is between about 5 and about 1,000 nucleotides, although in particular embodiments, a target polynucleotide as short as 4 nucleotides in length is contemplated. In other embodiments, a target polynucleotide of the present disclosure can be more than about 1,000 nucleotides in length. In some embodiments, a target polynucleotide can be between about 5 and about 200 nucleotides, or between about 50 and about 250 nucleotides in length. In particular embodiments, the length of a target polynucleotide is at or about, at least at or about, or no more than at or about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 300, 400, 500, 600, 700, 800, 900, or 1000 nucleotides. In some aspects, a target polynucleotide can be between about 50 and about 60, between about 60 and about 70, between about 70 and about 80, between about 80 and about 90, between about 90 and about 100, between about 100 and about 110, between about 110 and about 120, between about 120 and about 130, between about 130 and about 140, between about 140 and about 150, between about 150 and about 160, between about 160 and about 170, between about 170 and about 180, between about 180 and about 190, between about 190 and about 200, between about 200 and about 210, between about 210 and about 220, between about 220 and about 230, between about 230 and about 240, between about 240 and about 250, between about 250 and about 260, between about 260 and about 270, between about 270 and about 280, between about 280 and about 290, or between about 290 and about 300 in length. In some other aspects, the length of a target polynucleotide can be between about 300 and about 350, between about 350 and about 400, between about 400 and about 450, between about 450 and about 500, between about 500 and about 550, between about 550 and about 600, between about 600 and about 650, between about 650 and about 700, between about 700 and about 750, between about 750 and about 800, between about 800 and about 850, between about 850 and about 900, between about 900 and about 950, or between about 950 and about 1,000 nucleotides. The length of a target polynucleotide refers to the length of its primary structure, i.e., the linear sequence of nucleotides. A target polynucleotide of a suitable length can be triple-, double-, or single-stranded, or can form secondary or tertiary structures within the molecule (e.g., stem-loop or hairpin structures), or other higher-order structures with other molecules. In some embodiments, a target polynucleotide can be a short single-stranded polynucleotide, typically in the range of about 5 to about 1,000 or 5 to 200 or 5 to 100 nucleotides in length.

In some aspects, the target polynucleotide is a longer polynucleotide, such as an entire gene or gene segment. In some aspects, the target polynucleotide is a fragment of such a polynucleotide generated by restriction digest or other technique for generating fragmented polynucleotides, such as using any known restriction digest technique. Thus, in some embodiments, the provided methods include a step of fragmenting or digesting polynucleotides in a sample for capture and detection by the provided methods.

The target polynucleotide of the present disclosure may be a naturally occurring, recombinant, synthetic, or include one or more portions that are naturally occurring and one or more portions that are recombinant, synthesized, or modified with human intervention. A naturally occurring polynucleotide can carry particular modifications or be modified in particular ways, for example, depending on the physiological or pathological context. These modifications include, e.g., alkylation, methylation, phosphorylation, acetylation, uracil substitution, and capping. In certain aspects, the target polynucleotide also includes amplified products of itself, for example, as in a polymerase chain reaction.

In some aspects, the 5' terminus of the target polynucleotide is modified, for example, by phosphorylation. In certain aspects, phosphorylation of 5' ends facilitates or is required for enzymatic ligation of the target polynucleotide, as ligases need a 5'-phosphate and a 3'-OH to form a phosphodiester bond. In other aspects, the 3' terminus of the target polynucleotide can carry modifications that favor polymerization, e.g., extension of the target polynucleotide by a polymerase. Such a 3'-terminal modification can be a 3'-OH.

In certain embodiments, a target polynucleotide is a microRNA (miRNA). In certain aspects, the methods disclosed herein are used to detect or assay miRNAs, for example, as disease biomarkers for diagnostic and/or prognostic purposes, and/or as biomarkers to monitor responses to therapeutic interventions. miRNAs are small (typically 18-25 nucleotides) non-coding RNAs that are involved in regulating gene expression by binding to mRNA transcripts and influencing their stability or translation efficiency. miRNAs are detectable in blood, and have been shown to circulate within blood and appear to be relatively stable in the plasma and serum. In addition, expression profiles of some miRNAs, individually or as miRNA signatures, have been found to be altered in certain cancers and diseases. See, Mitchell, et al., 2008, "Circulating microRNAs as stable blood-based markers for cancer detection," *PNAS* 105: 10513-10518; Lawrie, et al., 2008, "Detection of elevated levels of tumour-associated micro-RNAs in serum of patients with diffuse large B-cell lymphoma," *Br J Haematol* 141:672-675; and Gilad, et al., 2008, "Serum microRNAs are promising novel biomarkers," *PLoS One* 3:e3148. A list of miRNAs for diagnostic and prognostic uses for prostate diseases is provided in U.S. Patent Application Publication No. US2010/0297652, the disclosure of which is herein incorporated by reference. In some aspects, genetic or epigenetic changes in miRNAs or their adjacent DNAs, for instance, mutations, deletions, insertions, or aberrant methylations, can affect miRNA expression and/or activity. Dysregulation of miRNAs and in turn pathways regulated by miRNAs can lead to tumorigenesis and cancer development. For example, circulating miRNAs have been linked to cancers, and have been validated as biomarkers for predicting lymph node metastasis in gastric cancer. See, Kim, et al., 2013, "Validation of circulating miRNA biomarkers for predicting lymph node metastasis in gastric cancer," *J Mol Diagn* 15:661-669. In the Kim, et al., study, synthetic miRNAs were used to generate a standard curve for circulating miRNAs, and linearity was confirmed within concentrations from 200 to 0.002 amol/μL. Various nucleic acid assay technologies can be used to identify and characterize miRNAs, including PCR-based assays. In certain embodiments, amplification techniques such as RT-PCR, qRT-PCR, ligase chain reaction (LCR), ligated activated transcription (LAT), or isothermal NASBA (nucleic acid sequence based amplification) can be used to amplify the miRNAs, in particularly low abundance miRNAs. It is also contemplated that the above amplification techniques can be used to amplify other target polynucleotides besides miRNAs.

In some embodiments, the target polynucleotide is RNA (for example, a miRNA or a mRNA fragment), and a sample containing the RNA target polynucleotide can be contacted with a template polynucleotide, for example, a synthetic DNA template polynucleotide, under conditions whereby the RNA target polynucleotide hybridizes to the template polynucleotide. A polymerase (e.g., a DNA polymerase) can then be used to extend the RNA target polynucleotide, thereby producing an extended target polynucleotide. When a target polynucleotide is an RNA and a DNA template polynucleotide and a DNA polymerase are used, the extended target polynucleotide includes an RNA portion (the RNA target polynucleotide) and a DNA portion extended by the polymerase. The nucleotide sequence of all or a portion of the extended target polynucleotide can then be determined, including the RNA target polynucleotide sequence. Alternatively, a RNA target polynucleotide can be first subjected to reverse transcription catalyzed by a reverse transcriptase, and converted into a DNA with complementary sequence to the RNA target polynucleotide. The complementary DNA sequence can then be detected and/or assayed by a method of the present disclosure. For example, random hexamer primers can be used to convert the RNAs in a sample, including the RNA target polynucleotide, to complementary DNAs. In yet another aspect, a template polynucleotide can be an RNA molecule, for example, an mRNA of a gene of interest. The RNA template polynucleotide can be used to assay DNA or RNA target polynucleotides. In this case, the DNA or RNA target polynucleotide can hybridize to the 5' terminus of the RNA template polynucleotide, and can be extended by a reverse transcriptase in the 3' to 5' direction to generate an extended target polynucleotide.

In some examples, the target polynucleotide is an antisense oligonucleotide. Thus, in some examples, the methods are used to detect the presence of antisense oligonucleotides, including those administered as disease treatments, such as may be useful in determining or confirming the dosage or half-life of antisense treatments. Thus, the provided methods in some contexts determine or confirm or analyze the pharmacodynamics, pharmacokinetics, serum half-life, delivery, or other aspect of an antisense oligonucleotide treatment.

In some embodiments, a target polynucleotide is single-stranded. In some aspects, a target polynucleotide can be a fragment of an RNA transcript, e.g., an mRNA produced from a genetic region or locus of interest. In other aspects, a target polynucleotide hybridizable to the genetic region or locus can be a sense strand or an anti sense strand. A sense strand, or coding strand, is the segment of double-stranded DNA running from 5' to 3' that is complementary to the antisense strand of DNA, which runs from 3' to 5'. The sense strand is the strand of DNA that has the same sequence as the mRNA, which takes the antisense strand as its template during transcription, and eventually typically undergoes translation into a protein. In certain embodiments, a sense strand target polynucleotide includes a sequence of an mRNA that may be produced from the genetic region or locus, with the exception that uracil of the mRNA sequence is substituted with thymine. In particular embodiments, template polynucleotides for the genetic region or locus of interest can be designed to be hybridizable to the sense or anti sense strand target polynucleotide.

In some aspects, the target polynucleotide is double-stranded. In one embodiment, a double-stranded target polynucleotide is converted to a single-stranded one by separating the strands or by removing one strand of the duplex. Strands of a duplex can be separated by thermal or chemical methods of disrupting inter-strand bonds. In certain embodiments, a duplex target polynucleotide can be denatured, using techniques and procedures known to one of skill in the art. In certain aspects, removing one strand allows recovery of the other strand and elimination of its complement. For example, one strategy for selectively removing one strand of a DNA duplex is to use exonuclease digestion, for example, 5' to 3' exonuclease digestion, where one strand is protected from attack by the exonuclease. U.S. Pat. No. 5,518,900 discloses a method of protecting a DNA strand by incorporating phosphorothioate nucleotide derivatives in the 5' end of the strand to be protected, rendering it resistant to exonuclease digestion, while the unprotected strand is preferentially digested by a 5' to 3' exonuclease.

In some embodiments, neither of the separated strands of a duplex target polynucleotide is removed from the sample, e.g., blood or plasma or sample prepared therefrom, before the sample is contacted with a template polynucleotide. In certain other aspects, in order to detect and/or assay both strands of a duplex target polynucleotide, a plurality of template polynucleotides can be used. For example, the plurality of template polynucleotides include at least one template polynucleotide hybridizable to one strand (e.g., the "sense" strand) of the duplex target polynucleotide and at least one template polynucleotide hybridizable to the other strand (e.g., the "antisense" strand) of the duplex target polynucleotide. In particular examples, at least 2, 3, 4, 5, 6, 7, 8, 9, 10, 11, 12, 13, 14, 15, 16, 17, 18, 19, 20, or more than 20 template polynucleotides are used. In other aspects, both strands of a duplex target polynucleotide can contribute to the amplification of a biomarker.

In some aspects, the target polynucleotide is a polynucleotide, such as fragmented nucleic acid, present in extracellular space as a result of cell shedding, and/or is a circulating polynucleotide. In some aspects, the target polynucleotide is fragmented DNA or other nucleic acid, such as fragmented DNA found in the extracellular space. Thus, in some aspects, the target polynucleotide is an extracellular nucleic acid, such as one present at elevated levels in a disease or condition or stage or state thereof, including but not limited to malignancies, infections, autoimmune and inflammatory diseases and conditions, and pregnancy, such as elevated fetal DNA or RNA in maternal blood, which may be used to determine gender identity, assess chromosomal abnormalities, and monitor pregnancy-associated complications. In other aspects, the target polynucleotide includes pathogen nucleic acids such as viral or bacterial nucleic acids. Such pathogenic nucleic acid may or may not be integrated into the genome of a cell of the subject from which the biological sample is obtained.

In certain embodiments, the target polynucleotide includes a plurality of target polynucleotides in a polynucleotide library. Polynucleotide libraries, for example genomic DNA libraries, are frequently generated and used for various purposes, e.g., genome sequencing, nuclei acid sequencing, screening, forensics, and disease diagnosis or prognosis. In certain aspects, polynucleotide libraries can be chemically synthesized, or generated by enzyme digestion or other nucleic acid cleavage methods. For example, the method disclosed herein can be used to detect or quantify a target polynucleotide in a library generated by digestion of genomic DNA. In one aspect, a target polynucleotide in the polynucleotide library can be preferentially enriched compared to other polynucleotides in the library, by a method of the present disclosure.

The methods typically include preparation or isolation of the target DNA from the biological sample, such as by any known or available method, e.g., magnetic beads, membrane filtration, solid-phase separation, e.g., using sephadex columns.

6. TEMPLATE POLYNUCLEOTIDES

The methods generally include providing one or more template polynucleotide to a sample containing or suspected of containing the target polynucleotide and/or biomarker of interest. Also provided are template polynucleotides, for example, for use in the provided methods, and compositions containing the same.

Thus, the template polynucleotide typically serves as a template for generating an extended target polynucleotide based on the sequence of the template polynucleotide. The template polynucleotide generally serves as a template in an extension reaction, whereby the target polynucleotide is extended, e.g., from its 3' end, by a polymerase, based on the sequence of the template polynucleotide. In some embodiments, the template polynucleotide serves as a template for ligation, whereby multiple target polynucleotides are ligated based on the sequence of the template.

In some embodiments, the template polynucleotide is a synthetic polynucleotide. In other embodiments, it is naturally occurring. In some aspects, the template polynucleotide is designed to hybridize to target polynucleotides, containing biomarkers of interest that are, or are suspected of being, present in the sample being assessed or a biological sample from which the sample is derived. As such, the template polynucleotides are often designed to contain some degree of complementarity or sequence identity to one or more genetic region or loci of interest, for which information about a biomarker or biomarkers is sought. For example, the template polynucleotide in some aspects is designed to contain or be complementary to all or part of a gene of interest or product (e.g., mRNA or cDNA) thereof, for example, where the biomarker includes or is a mutation or modification in the gene, the presence of a mutant or wild-type allele of the gene, or the presence of a product of the gene.

For example, the template polynucleotide can include a full length sequence of a gene of interest, e.g., BRAF gene sequence with exons and introns, or a fragment of the gene containing one or more "hot spots" corresponding to biomarker(s) of interest, such as hot spots for cancer-associated mutations. Target polynucleotides that are hybridizable to the template polynucleotide can then be detected, quantified, and/or otherwise assayed by a method of the present disclosure.

In some aspects, the template polynucleotide(s) is/are designed such that the methods detect or assay a single biomarker. In such examples, the target polynucleotide(s) identified, detected, or sequenced by the methods often includes multiple target polynucleotides, each containing the single biomarker.

In other examples, the template polynucleotide(s) is/are designed such that the methods detect or assay a plurality of biomarkers, such as a plurality of mutations, insertions, deletions, or modifications, which can be in the same or different genes. In such examples, the sample typically includes a first, second, etc., target polynucleotide, each containing one of the plurality of biomarkers. Each of the first, second, etc., target polynucleotides can include a plurality of polynucleotides, each with that particular biomarker. In some embodiments, a single target polynucleotide may have a plurality of the different biomarkers. When target polynucleotides having different biomarkers are present and detected, the methods typically involve providing template polynucleotides with complementarity to the respective target sequences, such as first, second, and so forth template polynucleotides, but in some embodiments, a single template can detect multiple biomarkers, such as multiple biomarkers within the same gene or portion or product thereof.

Figure 5:
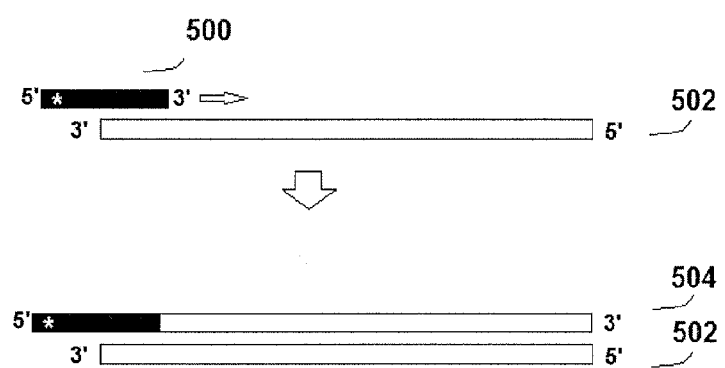
FIG. 5 depicts a method according to an example of the present disclosure. In this example, the target polynucleotide comprises a biomarker located in a region that does not share complementarity with the template polynucleotide.

In some examples, the target polynucleotide is capable of hybridizing to a region of the template polynucleotide toward the 3' end of or substantially at the 3' end of the template polynucleotide. In some aspects, a portion of the target polynucleotide containing the biomarker(s) of interest is in a region of the target polynucleotide (and thus, a region of the extended target polynucleotide) that shares complementarity with the template polynucleotide; in other aspects, it is in a region that does not share complementarity with the template polynucleotide. For example, as shown in FIG. 5, target polynucleotide 500 comprises a biomarker represented by an asterisk, which is in a region that does not share complementarity with template polynucleotide 502. An extended target polynucleotide 504 comprises the biomarker.

In some embodiments, the template polynucleotide contains one or more genetic regions or loci of interest. In some aspects, the template polynucleotide includes a full-length gene sequence with exons and introns, selected exons and/or introns, an mRNA sequence (with or without introns spliced out), a cDNA sequence, 3' or 5' untranslated sequences, or other portions of the gene or its transcript sequence. In some embodiments, the template polynucleotide includes "hot spots" for genetic variations or changes, for example, disease-associated mutations.

In certain aspects, all or a portion of the template polynucleotide is chemically synthesized, for example, using a known polynucleotide synthesis technique. In other aspects, all or a portion of the template polynucleotide is recombinantly produced. In some aspects, the template polynucleotide is isolated and purified from a biological sample, for example, by restriction enzyme digestion of genomic DNA followed by isolation and purification of the desired template polynucleotide sequence (e.g., by electrophoresis and Southern blotting).

In some embodiments, the sample containing or suspected of containing the target polynucleotide is contacted with the template polynucleotide comprising a region or locus of interest, under conditions that allow the target polynucleotide to hybridize to the template polynucleotide. Thus, in some embodiments, the template polynucleotide is capable of hybridizing, e.g., under stringent conditions, to a target polynucleotide containing the biomarker of interest or having the gene or region or locus or loci of interest.

In some embodiments, the template polynucleotide is substantially complementary to the target polynucleotide, such that the two are hybridizable to each other, for example, under stringent hybridization conditions. A target polynucleotide may pair with a region on the template polynucleotide with 100%, at least about 99%, at least about 95%, at least about 90%, at least about 85%, at least about 80%, at least about 75%, at least about 70%, at least about 65%, at least about 60%, at least about 55%, or at least about 50% sequence complementarity. In some embodiments, a target polynucleotide can hybridize to the template polynucleotide with less than about 25%, less than about 15%, less than about 5%, or no mismatches between opposed nucleotides. Although hybridization between the target and template polynucleotides under conditions of high stringency are typical, lower stringency conditions are also contemplated and can be used.

In certain aspects, the target polynucleotide hybridizes to any region of the template polynucleotide. In some examples, for a DNA template polynucleotide, the target polynucleotide (which can be DNA or RNA) hybridizes to (and shares complementarity with) a region substantially at the 3' terminus of the DNA template polynucleotide (e.g., within the 5, 10, 15, 20, 25, 30, 35, 40, 45, 50, 55, 60, 65, 70, 75, 80, 90, or 100 3'-most nucleotides or within the 1, 2, 3, 4, 5, 10, 15, 20, 25, 30, 35, 40, 45, or 50% 3'-most portion of the template polynucleotide), such that the target polynucleotide can be extended by a DNA polymerase in the 5' to 3' direction. In some aspects, the target polynucleotide hybridizes to a region substantially at the 5' terminus of the template polynucleotide (e.g., an RNA template polynucleotide) (e.g., within the 5, 10, 15, 20, 25, 30, 35, 40, 45, 50, 55, 60, 65, 70, 75, 80, 90, or 100 5'-most nucleotides or within the 1, 2, 3, 4, 5, 10, 15, 20, 25, 30, 35, 40, 45, or 50% 5'-most portion of the template polynucleotide), wherein the target polynucleotide can be extended by a reverse transcriptase in the 3' to 5' direction.

In certain aspects, the target polynucleotide hybridizes with the template polynucleotide to form a blunt end (e.g., as shown in FIG. 1 for target polynucleotide 102), a 3' overhang on the template (e.g., as shown in FIG. 1 for target polynucleotide 104), and/or a 5' overhang on the target (e.g., as shown in FIG. 1 for target polynucleotide 106). In some embodiments, the target polynucleotide includes a plurality of target polynucleotides, e.g., each containing the biomarker of interest. In such embodiments, the plurality can include those that hybridize to form a blunt end, a 3' overhang and/or a 5' overhang. The target polynucleotide generally is shorter in sequence than the template polynucleotide. The sequence containing the biomarker, e.g., the sequence of the target polynucleotide containing the biomarker often varies in comparison with the sequence of the template polynucleotide. For example, the biomarker may be or contain a point mutation, deletion, insertion, or modification as compared with the corresponding or complementary sequence of the template polynucleotide.

Figure 2:
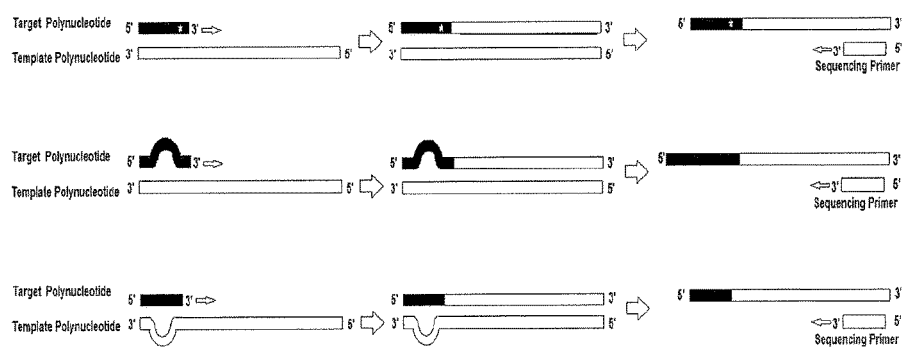
FIG. 2 depicts various exemplary target polynucleotides for use with methods of the present disclosure. As shown in the top panel, in some examples, the target polynucleotide includes a mutation or single nucleotide mismatch compared to the template polynucleotide, indicated by the asterisk; as shown in the middle and bottom panels, it may in some examples include an insertion or deletion compared to the template polynucleotide. Such differences may form part of the biomarker and in some aspects are identified or confirmed by methods provided herein.

Thus, mismatch, deletion, and/or insertion when comparing the target polynucleotide and template polynucleotide pair, and detection thereof by the provided methods and systems, are envisaged, for example, as shown in FIGS. 2-3. In certain embodiments, the target polynucleotide contains one or more point mutations as compared to, and is hybridizable to, the template polynucleotide. In the example shown in the top panel of FIG. 2, an extended target polynucleotide is generated from the target polynucleotide sequence which includes as the biomarker point mutation indicated by the asterisk. In one aspect, the point mutation may be known to be associated with a particular disease or condition. In some such aspects, the methods are used to determine whether the biomarker, e.g., genetic variation, e.g., point mutation, is present in the sample, such as a biological sample from a subject or population having or suspecting of having the disease or condition. If the variation is detected in the sample, in one embodiment, the provided methods include quantifying the concentration of polynucleotides, e.g., target polynucleotides, carrying the variation in the sample, and/or frequency of the variation in the subject or population. In some embodiments, the particular biomarker be unknown, or may have not been known to associate with a particular disease or condition, at the outset of the methods. Detection of a biomarker such as a point mutation in a subject or population having or suspecting of having a disease or condition, but not in a normal control subject or population, can indicate that the biomarker is associated with the disease or condition. Similarly, in one aspect, the target polynucleotide contains an insertion or a deletion and is hybridizable to the template polynucleotide, for example as shown in FIG. 2 middle and bottom panels, respectively. Thus, in some examples, an extended target polynucleotide including the target polynucleotide sequence containing the insertion or the deletion is generated. In some aspects, detecting the biomarker, e.g., by sequencing the extended target polynucleotide, determines the sequence of the insertion or the deletion and/or determines the presence or absence of the insertion or deletion in the sample organism or population.

The template polynucleotide typically is longer in sequence than the target polynucleotide. In some embodiments, the template polynucleotide itself is not extended by the polymerase. In some aspects, the template polynucleotide is engineered in such a way so as to prevent extension by the polymerase under conditions whereby the target polynucleotide is extended. For example, the template polynucleotide, e.g., a DNA template polynucleotide, can be blocked at its 3' end, thereby preventing extension of the DNA template polynucleotide in the 5' to 3' direction. In particular embodiments, the 3' terminus of the DNA template polynucleotide can be dephosphorylated or can carry other modifications that prevent polymerization, e.g., extension of the template polynucleotide by a polymerase. Alternatively, the template polynucleotide can be circular, such that the template polynucleotide itself is not extendable by the polymerase. In yet other embodiments, the 5' terminus of the template polynucleotide is modified, for example, by phosphorylation. In certain aspects, phosphorylation of the 5' terminus facilitates enzymatic ligation of the template polynucleotide, for example, to a second template polynucleotide hybridized to the same template polynucleotide In certain embodiments, the template polynucleotide may include one or more uracil bases or deoxyuridine (dU) moieties. In one aspect, dUTP can be incorporated into the template polynucleotide, for example, by including dUTP or substituting dUTP for dTTP in a PCR reaction for template polynucleotide amplification, or during synthesis of a primer used for making, amplifying, or modifying the template polynucleotide. A uracil DNA glycosylase (UDG) can be used to cleave the glycosidic bond between the uracil base and the deoxyribose sugar. See, Duncan, 1981, *The Enzymes* 14:565, ed.: Boyer P. Double and single-stranded dU-containing DNA are substrates for UDG, whereas RNA and normal dT-containing DNA are not. The enzyme does not act upon free dUTP or free deoxyuridine. After UDG cleaves the uracil base from the phosphodiester backbone, the resulting apyrimidinic sites block replication by DNA polymerases, and are labile to acid/base hydrolysis. In one aspect, UDG-mediated digestion can be used to remove unwanted DNA species from a sample or a reaction mixture of the present disclosure. For example, when RNA target polynucleotides in a sample are to be detected and/or assayed, DNA in the sample can be incorporated with uracil and subjected to UDG-mediated digestion to remove the DNA. In another embodiment, a dU-containing template polynucleotide can be removed by UDG-mediated digestion, to minimize interference with determining the sequences of extended target polynucleotides. UDG-mediated digestion of a template polynucleotide can be performed before, during, or even after sequence determination, e.g., for analysis or procedures downstream of sequence determination.

In certain aspects, the template polynucleotide is used to detect or assay a single species of target polynucleotide(s) in a sample—which single target polynucleotide species can include a plurality of target polynucleotides, each containing the same target sequence or biomarker, e.g., genetic variation, of interest. In other aspects, one or more template polynucleotides is used to detect or assay multiple target sequences or biomarkers, e.g., genetic variations, in a sample (such as those of multiple target polynucleotide species). In one such example, the method includes assessing or detecting a first, second, and optionally third, and so-forth, target polynucleotides in the sample, where each of the first, second, etc., target polynucleotides contains a distinct biomarker, e.g., genetic variation, or target sequence. In some aspects, the template polynucleotide includes at least two portions, and each of the at least two portions is hybridizable to single target sequences or variations or multiples target sequences or variations, or both. It is within the present disclosure that a plurality of template polynucleotides can be used in a method disclosed herein. For example, each of the plurality of template polynucleotides can include the same genetic region or locus of interest. In particular examples, at least 2, 3, 4, 5, 6, 7, 8, 9, 10, 11, 12, 13, 14, 15, 16, 17, 18, 19, 20, or more than 20 template polynucleotides including the same genetic region or locus of interest are used. In other embodiments, a plurality of template polynucleotides, at least two of which include different regions or loci of interest, are used to detect target polynucleotides for the different regions or loci of interest. In particular examples, at least 2, 3, 4, 5, 6, 7, 8, 9, 10, 11, 12, 13, 14, 15, 16, 17, 18, 19, 20, or more than 20 template polynucleotides comprising different regions or loci of interest are used.

A template polynucleotide can be single-stranded or double-stranded. For a double-stranded template polynucleotide, the two strands can be separated and in certain embodiments, either single strand can be used as a single-stranded template polynucleotide. In this case, the two single-stranded template polynucleotides with sequence complementarity are hybridizable to the sense or antisense strand target polynucleotide, respectively, for a genetic region or locus of interest. In certain embodiments, the 3'-termini of a double-stranded DNA template polynucleotide can be blocked to prevent extension of the template polynucleotide strands in the 5' to 3' direction.

Figure 4:
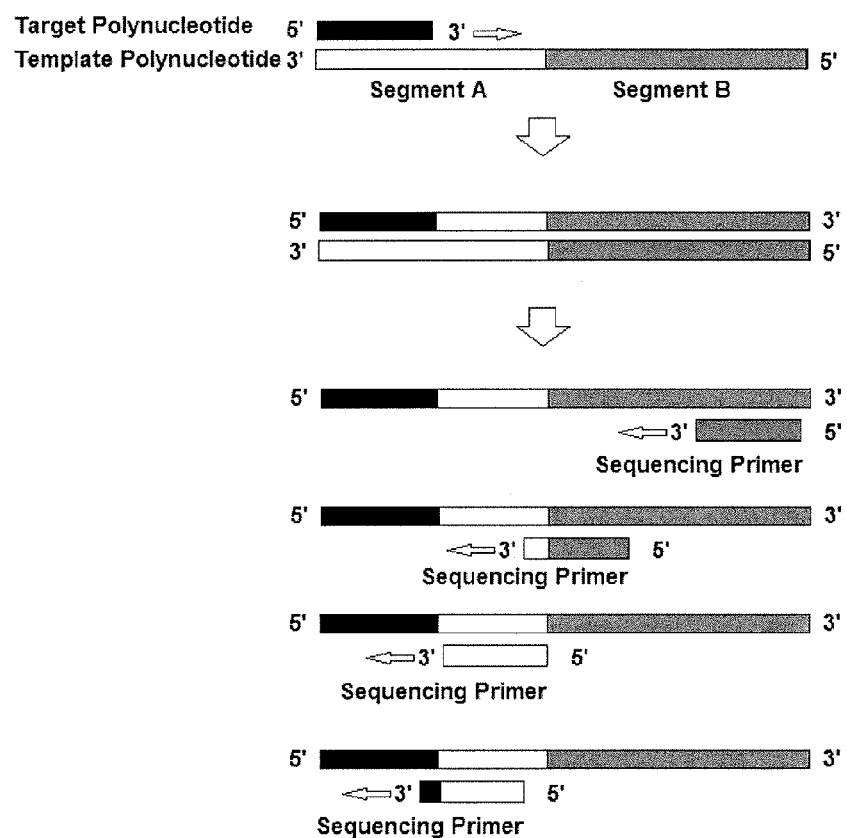
FIG. 4 depicts a method according to an example of the present disclosure. The template polynucleotide shown includes two segments, Segment A (a first segment) and Segment B (a second segment). Segment A is complementary to and hybridizable to the target polynucleotide. Under conditions in which the target polynucleotide hybridizes to Segment A, the target polynucleotide does not hybridize to Segment B. The extended target polynucleotide includes a portion complementary to the first segment and a portion complementary to the second segment. As shown, one or more primer hybridizable to the portion of the extended target polynucleotide that is complementary to Segment A and/or to the portion of the extended target polynucleotide that is complementary to Segment B can be used to amplify and/or sequence the extended target polynucleotide. Whereas the primers in FIG. 4 are labeled "sequencing primer," in some embodiments, such primers are alternatively used for amplification.

In some aspects, the template polynucleotide includes a first segment that is hybridizable to the target polynucleotide and/or contains complementarity or identity to the locus or region of interest, and a second segment that does not hybridize to the target polynucleotide under conditions that allow hybridization of the first segment to the target polynucleotide and/or does not contain complementarity or identity (or substantial complementarity or identity) to the region or locus of interest. For example, in the case of a biomarker that is in or is a gene or gene product, the first segment may contain identity or complementarity to the gene or segment thereof or product or segment thereof, while the second segment does not. In certain embodiments, the second segment is at the 5' of the first segment. For example as shown in FIG. 4, Segment A and Segment B represents a first and a second segment, respectively. In this case, a target polynucleotide is hybridizable to Segment A, and the target polynucleotide is extended by a polymerase to generate an extended target polynucleotide, which includes a portion complementary to Segment A (first segment) and a portion complementary to Segment B (second segment). In certain embodiments, one or both of the first and second segments can be chemically synthesized, recombinantly produced, or generated by nucleic acid cleavage (e.g., restriction enzyme digestion), e.g., from genomic DNA, RNA, or cDNA.

In some embodiments, the template polynucleotide has a sequence of SEQ ID NO:1 or SEQ ID NO:8, or contains at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% identity to SEQ ID NO:1 or 8.

7. EXTENSION AND LIGATION

The methods generally capture and detect target polynucleotides, typically polynucleotide fragments, which contain the biomarker(s) of interest and are present in a sample. Capture is typically carried out by generating an extended target polynucleotide containing sequence from the target polynucleotide and additional sequence, generally based on the sequence of the template polynucleotide.

Extension Using Biomarker-Containing Target Polynucleotides as Primers

In some examples, the capture is carried out by performing an extension reaction in which the target polynucleotides, e.g., fragments, serve as primers. In some embodiments, the target polynucleotide, e.g., fragmented polynucleotide, e.g., DNA, present in the sample serves as a primer and is extended by a polymerase, based on the sequence of a template polynucleotide. The template polynucleotide generally is provided to the sample under conditions whereby it will hybridize to the target polynucleotide (e.g., under conditions where it will hybridize to a sequence containing a region or locus of interest), typically in the presence of an agent for extension (e.g., polymerase). In this aspect, the target polynucleotide hybridizes to the template polynucleotide and is extended based on the sequence of the template polynucleotide.

Thus, in some embodiments, an agent for extension (e.g., a polymerase) is provided under conditions that permit extension of the target polynucleotide (e.g., when hybridized to the template polynucleotide) by the polymerase, to produce an extended target polynucleotide. In such aspects, the target polynucleotide serves as a primer, for extension of the target polynucleotide according to the sequence of the template polynucleotide. In this way, the provided methods in some aspects differ from conventional PCR methods, in which the template sequence contains the sequence of interest, unknown sequence, or sequence to be detected or determined, e.g., from conventional methods in which the template contains the biomarker(s). In such conventional PCR methods, it is often this unknown sequence of interest that is copied and determined by hybridization to and extension of primers (generally having known sequences) based on the sequence of the template (generally unknown or containing a biomarker not known to be present). Thus, in some embodiments of the provided method, the target polynucleotide (the primer) includes a biomarker, which is to be detected or determined, while the template polynucleotide sequence is known and can be designed for detecting or determining particular target polynucleotide sequences.

Agents for Extension and Extension Process

The agent for extension of the target polynucleotide may be any compound or system which will function to accomplish the synthesis of "primer" extension products, including enzymes. Suitable enzymes for this purpose include, for example, *E. coli* DNA polymerase I, Klenow fragment of *E. coli* DNA polymerase, polymerase muteins, reverse transcriptase, other enzymes, including heat-stable enzymes (i.e., those enzymes which perform primer extension after being subjected to temperatures sufficiently elevated to cause denaturation), such as Taq polymerase. The suitable enzyme will facilitate combination of the nucleotides in the proper manner to form the extended target polynucleotides which include complementary sequences to the template polynucleotide. Generally, the synthesis/extension will be initiated at the 3' end of each target polynucleotide hybridized to the template and proceed in the 5' direction along the template polynucleotide, until synthesis terminates, producing molecules of different lengths. In some embodiments, the synthesis/extension can proceed to the 5' end of the template polynucleotide, as shown in FIGS. 1-4. It is, however, envisaged that in certain embodiments, extension of the target polynucleotide can terminate at any position before reaching the 5' end of the template polynucleotide.

The newly synthesized strand (the extended target polynucleotide comprising the target polynucleotide and a sequence produced by nucleotide synthesis and complementary to the template polynucleotide) and the template polynucleotide form a double-stranded molecule. In certain embodiments, the newly synthesized double-stranded molecule is subjected to denaturing conditions to provide single-stranded molecules, using procedures known to one of skill in the art. For example, heating to about 90°–100° C. for from about 1 to about 10 minutes, such as from about 1 to about 4 minutes, is sufficient to denature double-stranded polynucleotides. The single-stranded template polynucleotide can be used in the next round of nucleotide synthesis, to allow more target polynucleotides in the sample to bind in order to be extended.

Ligation Using Synthetic Template

In some embodiments, the extended target polynucleotide is generated by ligation. For example, in some embodiments, the template polynucleotide is added to the sample containing target polynucleotides under conditions (e.g., in the presence of a ligase) whereby the target polynucleotides hybridize to the template polynucleotide and are ligated to one another, such as by template-driven ligation, to form the extended target polynucleotide. In some aspects of such embodiments, one or more of the plurality of target polynucleotides is extended by a polymerase.

Figure 7:
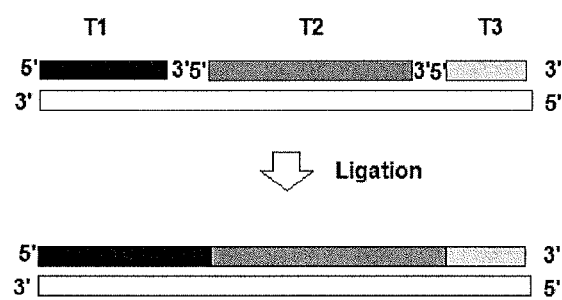
FIG. 7 depicts a method according to an example of the present disclosure. In this example, target polynucleotides T1, T2, and T3 hybridize to the same template polynucleotide. Target polynucleotide T1 can be ligated to target polynucleotide T2, and target polynucleotide T2 can be ligated to target polynucleotide T3, to form an extended target polynucleotide. Extension of the individual target polynucleotides by a polymerase is optional.

In certain embodiments, a plurality of target polynucleotides hybridize to the same template polynucleotide molecule. In one aspect, one or more of the plurality of target polynucleotides are extended by a polymerase. In another aspect, the plurality of target polynucleotides hybridized to the same template polynucleotide molecule are ligated to form an extended target polynucleotide. In certain embodiments, one or more of the plurality of target polynucleotides are extended before ligation to another target polynucleotide hybridized to the same template polynucleotide. For example, as shown in FIG. 7, target polynucleotides T1, T2, and T3 hybridize to the same template polynucleotide. Target polynucleotide T1 can be ligated to target polynucleotide T2, and target polynucleotide T2 can be ligated to target polynucleotide T3. Both ligations can be done with or without extension of the target polynucleotides. In one aspect, the ligated target polynucleotides (which form an extended target polynucleotide, although in some embodiments, no extension of any of the individual target polynucleotide is necessary) can be further extended by a polymerase.

8. AMPLIFICATION AND PROCESSING

In some embodiments, the extended target polynucleotide is amplified. In some aspects, the amplification is carried out prior to sequence determination, for example, to obtain sufficient copies of the biomarker of interest for detection, identification, or sequencing. In one embodiment, a primer hybridizable to the extended target polynucleotide is used to asymmetrically amplify all or a portion of the extended target polynucleotide. In the example shown in FIG. 4, the shown primers may be used to amplify the extended target polynucleotide (although labeled "sequencing primers," primers directed to these same regions may be used for amplification).

In one aspect, the template polynucleotide includes a first segment that is hybridizable to the target polynucleotide, and a second segment that does not hybridize to the target polynucleotide under conditions that allow hybridization of the first segment to the target polynucleotide. In this case, amplification of all or a portion of the extended target polynucleotide can be carried out by using: (1) a primer hybridizable to the portion complementary to the first segment; (2) a primer hybridizable to the portion complementary to the second segment; or (3) a primer hybridizable to both the portion complementary to the first and second segments of the template polynucleotide. Specifically in FIG. 4, the extended target polynucleotide can be amplified using a primer hybridizable to the portion complementary to Segment B, a primer hybridizable to the portion complementary to Segment A, or a primer hybridizable to both the portion complementary to Segment A and the portion complementary to Segment B.

In other embodiments, both strands of a duplex target polynucleotide can contribute to the amplification of the biomarker(s).

In some embodiments, a primer that has homology to the 5'-terminus of a target polynucleotide can be used to amplify the extended target polynucleotide. For example, a primer pair including a primer hybridizable to the 3'-terminus of the extended target polynucleotide, and a primer that has homology to the 5'-terminus of the target polynucleotide, can be used to symmetrically amplify the extended target polynucleotide. In some aspects, such a primer is designed based on a region or locus of interest that may or may not contain the biomarker of interest, for example, a primer designed to bind to a gene of interest, a mutation in which is associated with a disease or condition. In some examples, the primer may be designed to have complementarity or identity to a region of the gene, region, or locus that is not likely to or is known not to contain the biomarker (e.g., a region of the gene other than the position of the mutation, deletion, or insertion of interest). In some examples, the primer is designed not to share complementarity with the template, such that the target polynucleotide contains complementarity or identity to the primer at its 5' end and complementarity to the template polynucleotide at its 3' end.

Figure 6:
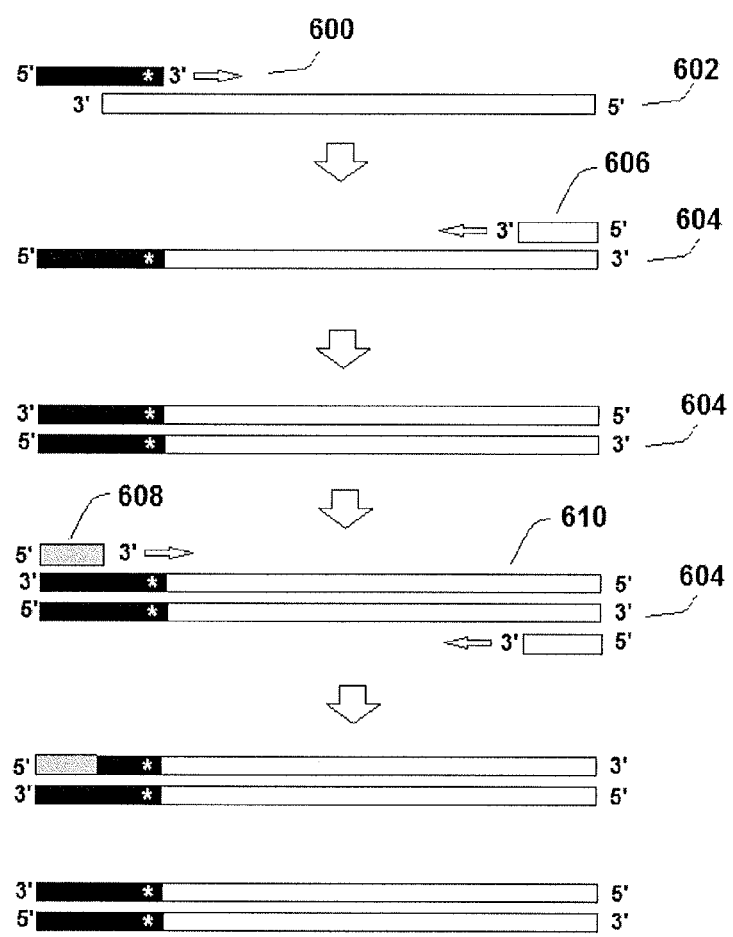
FIG. 6 depicts a method according to an example of the present disclosure. A primer pair, including a primer with partial homology to (homology to the 5'-terminus of) a target polynucleotide and a primer hybridizable to the 3'-terminus of an extended target polynucleotide, is used to amplify a sequence containing a biomarker, including the mutation or single nucleotide mismatch indicated by the asterisk. In other aspects, the biomarker includes an insertion or deletion.

One example of such a symmetrical amplification is shown in FIG. 6. In this example, target polynucleotide 600 is hybridizable to template polynucleotide 602 and is extended in the 5' to 3' direction by a polymerase to generate extended target polynucleotide 604. Target polynucleotide 600 contains a mutation indicated by the asterisk. Primer 606, which is hybridizable to the 3'-terminus of extended target polynucleotide 604, replicates the extended target polynucleotide. Primer 608 has homology to the 5'-terminus of target polynucleotide 600, and is hybridizable to a replicated extended target polynucleotide 610. In this example, primer 608 has partial homology to the target polynucleotide 600. Typically, the partial homology is to a region of the target polynucleotide that does not share complementarity with the template polynucleotide, e.g., the 5' terminus of the target polynucleotide. Thus, the primer pair (primers 606 and 608) can be used to symmetrically amplify extended target polynucleotides containing the mutation.

In some embodiments, amplification techniques such as rolling circle amplification (RCA) and circle-to-circle amplification (C2CA) may be used. RCA is a linear-isothermal process in the presence of certain DNA polymerases, using an ssDNA mini-circle as a template. See, Fire and Xu, 1995, *Proc. Natl. Acad. Sci.*, 92:4641-4645; Daubendiek, et al., 1995, *J. Am. Chem. Soc.* 117:77818-7819. In certain aspects, a polynucleotide sequence can be replicated about 500 to 1000 times, depending on the amplification time. In one embodiment, an extended target polynucleotide can be ligated to form a DNA circle by a DNA ligase, e.g., guided by a primer comprising both a sequence hybridizable to the 3'-terminus of the extended target polynucleotide and a sequence hybridizable to the 5'-terminus of the extended target polynucleotide. In certain embodiments, phi29 DNA polymerase can then be used to extend the primer, to form a long ssDNA containing a number of sequences complementary to the initial DNA circle formed by the extended target polynucleotide. C2CA is based on RCA, and can include three steps: replication, monomerization and ligation. The original circular DNA is considered as the positive polarity. After one step of replication (RCA reaction), the product is converted into the opposite polarity. Restriction oligos with the positive polarity ($RO^+$) can form duplex regions with the RCA product, and the duplex regions can be cleaved by restriction enzymes to generate monomers. Then the monomers can be guided into a ligation step and circularized. These circles serve as the templates for the next round of RCA, primed by the $RO^+$. See, Dahl, et al., 2004, *Proc. Natl. Acad. Sci.*, 101:4548-4553. The process can be further repeated to produce around 100-fold higher concentration of target sequences than conventional PCR.

In some embodiments, a sample following extension and/or amplification of the target polynucleotide is cleaned, or enriched for the extended target polynucleotide, to facilitate identification of the target polynucleotide sequence. For example, double and single-stranded dU-containing DNA in the sample can be removed by uracil DNA glycosylase (UDG) digestion. As disclosed supra, dU can be incorporated into the template polynucleotide, which can be digested with UDG upon completion of extension and/or amplification of the target polynucleotide. Other methods can be used to clean and/or enrich for the extended target polynucleotide. These methods include column purification and membrane-based size exclusion, among others. Exemplary methods of polynucleotide purification are disclosed in U.S. Pat. No. 4,923,978 (purification through a hydroxylated support), U.S. Pat. No. 4,935,342 (anion exchange columns), U.S. Pat. No. 4,946,952 (DNA isolation by precipitation with water-soluble ketones), and U.S. Pat. No. 4,900,677 (DNA purification using chaotropes).

9. IDENTIFICATION, DETECTION, AND SEQUENCING

The methods generally include a detection or identification step, for example, whereby the presence or absence of the biomarker in the sample or biological sample or subject from which the sample is derived.

In certain embodiments, the target polynucleotide or extended target polynucleotide is identified. In some aspects, the identification includes determining the sequence of the extended target polynucleotide. Thus, in some embodiments, the determining includes performing nucleotide sequencing on the extended target polynucleotide. Thus, in certain embodiments, the nucleotide sequence of all or a portion of the extended target polynucleotide is determined, for example, by sequencing technologies known to one of skill in the art, thereby detecting the biomarker in the sample. Suitable sequencing or sequence determination techniques include but are limited to mass spectroscopy (e.g., matrix-assisted laser desorption/ionization-time of flight mass spectrometry (MALDI-TOF), LC-MS/MS, and TOF/TOF™ LC/MS/MS), nuclear magnetic resonance imaging, and nucleic acid sequencing. Exemplary sequencing techniques can be found in U.S. Patent Application Publication No. 2008/0220434, incorporated herein by reference for all purposes. In FIG. 1, for example, a sequencing primer hybridizable to the 3' end of an extended target polynucleotide can be used to sequence all or a portion of the extended target polynucleotide, such that the target polynucleotide sequence including any biomarker therein can be determined. In certain embodiments, since the template sequence is known, and the extended target polynucleotide includes a sequence complementary to the 5' end of the template, sequencing primers hybridizable to various regions of the extended target polynucleotide can be designed and used.

In aspects of the provided methods, the extended target polynucleotide can be subjected to high-throughput, next-generation sequencing, and highly parallel next-generation sequencing methods are used to confirm the sequence of the extended target polynucleotide. Suitable next-generation sequencing technologies include but are not limited to SOLiD™ technology (Life Technologies, Inc.) or Genome Analyzer (Illumina, Inc.). Such next-generation sequencing methods can be carried out, for example, using a one pass sequencing method or using paired-end sequencing. Next generation sequencing methods include, but are not limited to, hybridization-based methods, such as disclosed in, e.g., Drmanac, U.S. Pat. Nos. 6,864,052; 6,309,824; and 6,401,267; and Drmanac, et al., U.S. Patent Application Publication No. 2005/0191656; sequencing-by-synthesis methods, e.g., U.S. Pat. Nos. 6,210,891; 6,828,100; 6,969,488; 6,897,023; 6,833,246; 6,911,345; 6,787,308; 7,297,518; 7,462,449 and 7,501,245; U.S. Patent Application Publication Nos. 2011/0059436; 2004/0106110; 2003/0064398; and 2003/0022207; Ronaghi, et al., *Science*, 281:363-365 (1998); and Li, et al., *Proc. Natl. Acad. Sci.*, 100:414-419 (2003); ligation-based methods, e.g., U.S. Pat. Nos. 5,912,148 and 6,130,073; and U.S. Patent Application Nos. 2010/0105052, 2007/0207482 and 2009/0018024; nanopore sequencing, e.g., U.S. Patent Application Nos. 2007/0036511; 2008/0032301; 2008/0128627; 2009/0082212; and Soni and Meller, *Clin Chem* 53:1996-2001 (2007), as well as other methods, e.g., U.S. Patent Application Nos. 2011/0033854; 2009/0264299; 2009/0155781; and 2009/0005252; also, see, McKernan, et al., *Genome Res.* 19:1527-1541 (2009) and Bentley, et al., *Nature* 456:53-59 (2008), all of which are incorporated herein in their entirety for all purposes.

Also provided are sequencing methods, for use alone or in combination with the provided extension or ligation methods.

Multiplex Sequencing

In some aspects, the provided methods include multiplexing (e.g., detecting or sequence multiple loci simultaneously), including multiplex or multi-loci sequencing methods. In some embodiments, multiple (first, second, etc.) polynucleotides with distinct sequences are sequenced by employing multiple (first, second, etc.) respective sequencing primers, where a second sequencing primer is designed to be larger in size and/or molecular weight than any of the products generated by extension using the first sequencing primer, and chain-terminating nucleotides, where, for example, Sanger sequencing is used to determine sequence. In one aspect, products generated by the different sequencing primers thus are distinguished, e.g., separated, based on size or molecular weight. In this aspect, the provided methods are capable of simultaneously sequencing multiple polynucleotides with a plurality of biomarkers.

Thus, in some embodiments, the sequences of a plurality of polynucleotides (e.g., plurality of extended target polynucleotides, such as those containing a respective plurality of biomarkers) are determined. For example, if the plurality of polynucleotides include a first and second extended target polynucleotides, the methods in some aspects include performing Sanger-based sequencing on each of those extended target polynucleotides, using first and second sequencing primers, designed such that the second sequencing primer is larger than the largest of the products generated by extension of the first sequencing primer. In such examples, the products of such extension can be differentiated, e.g., separated, from each other, such that two different biomarkers may be assessed simultaneously.

Therefore, a template polynucleotide comprising two or more different regions or loci of interest, or a plurality of template polynucleotides, at least two of which include different regions or loci of interest, can be used to detect or assay a plurality of target polypeptides for the different regions or loci, for example, using a multiplex sequencing method to sequence the extended target polynucleotides for the different regions or loci.

In some embodiments, the provided methods include:

(a) contacting the sample with a first template polynucleotide, under conditions whereby a first target polynucleotide in the sample hybridizes to the first template polynucleotide, wherein the first target polynucleotide includes a first biomarker, and contacting the sample with a second template polynucleotide hybridizable to the second target polynucleotide, under conditions whereby the second target polynucleotide hybridizes to the second template polynucleotide, wherein the second target polynucleotide includes a second biomarker;

(b) providing a polymerase, under conditions that permit extension of the first and second target polynucleotides by the polymerase (or performing ligation reactions whereby the first and second target polynucleotides are ligated to other target polynucleotides), thereby producing a first and a second extended target polynucleotide, respectively; and (c) determining the nucleotide sequence of all or a portion of the first and second extended target polynucleotides comprising the first and second biomarkers, respectively, thereby detecting presence of the biomarkers in the sample, where in some aspects, the determining is by multi-loci or multiplex sequencing as described herein. In some cases, the first biomarker is or corresponds to a mutant allele or portion of a gene or locus, and the second biomarker corresponds to a wild-type or normal allele or portion. In other cases, the first and second biomarkers each correspond to different mutations or genetic or epigenetic variations, e.g., in the same or different genes.

In some embodiments, the multiplexing sequencing, for example, for the determining step of the methods, includes combining in a reaction mixture the first and second (and optionally, third, fourth, etc.) extended target polynucleotides, first and second (and optionally third, fourth, etc.) labeled sequencing primers hybridizable respectively to the first and second (and optionally third, fourth, etc.) extended target polynucleotides, a polymerase, nucleotides, and a chain-terminating nucleotide, under conditions that permit hybridization of the first and second (optionally more) sequencing primers to the first and second (optionally more) extended target polynucleotides, respectively, and extension of the first and second (optionally more) sequencing primers, wherein the periodic incorporation of the chain-terminating nucleotide by the polymerase terminates polymerization, thereby producing a pool of first target products of a plurality of lengths having complementarity to the first extended target polynucleotide and a pool of second target products of a plurality of lengths having complementarity to the second extended target polynucleotide (and optionally, so forth), wherein the second sequencing primer has a molecular weight at least as large as or larger than the largest of the first target products, whereby each of the second target products has a molecular weight greater than each of the first target products, or wherein the second sequencing primer has a molecular weight at least as large as or larger than the first extended target polynucleotide. The products then generally are differentiated, e.g., separated, based on differences in size or molecular weight. In particular embodiments, the first target products are separated from the second target products, and optionally, third, fourth, etc. target products.

Figure 8:
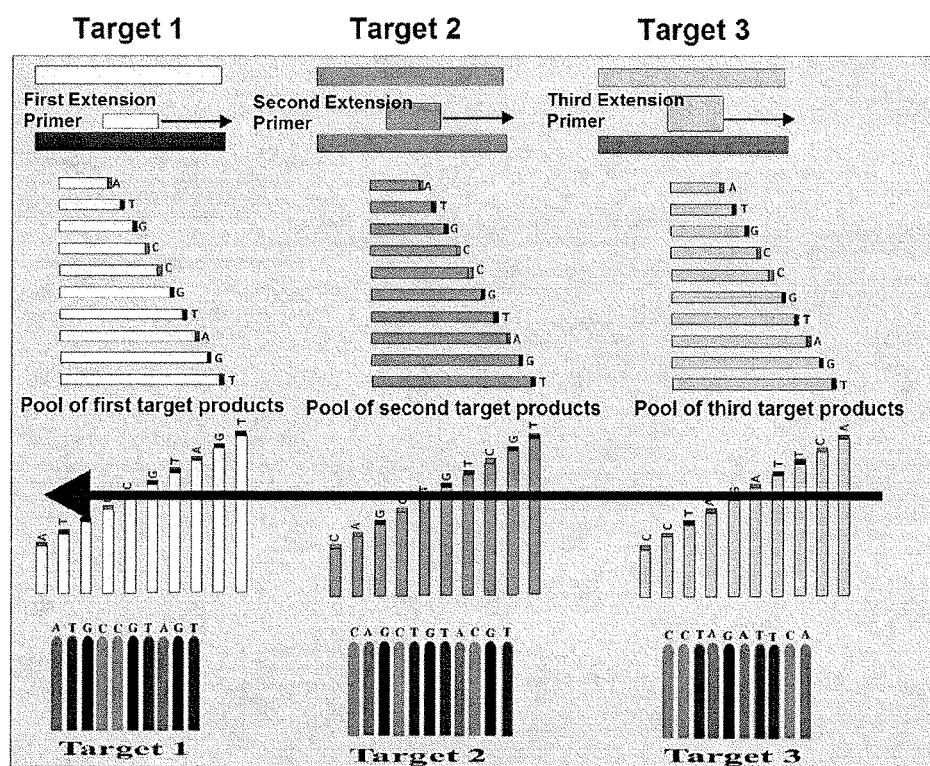
FIG. 8 depicts an exemplary multiplex sequencing process for use with the provided methods. First, second, and third polynucleotides (labeled "Target 1," "Target 2," and "Target 3," respectively) are combined with first, second, and third extension primers, respectively. The combining is done in combination with polymerase, nucleotides, and chain-terminating nucleotides, to generate pools of first, second, and third target products, respectively, each pool containing products of varying lengths. Sanger sequencing is used to determine sequence. Products are differentiated by molecular weight. As shown in this example, the molecular weight of each of the third target products is higher than that of the second target products; the molecular weight of each of the second target products is higher than that of each of the first target products. In some aspects, this sequencing process is used in connection with the provided methods, such as those shown in one or more of FIGS. 1-7.

In an example shown in FIG. 8, first, second, and third polynucleotides (labeled "Target 1," "Target 2," and "Target 3," respectively) are combined with first, second, and third sequencing primers, respectively. This is done in combination with polymerase, nucleotides, and chain-terminating nucleotides, to generate pools of first, second, and third target products, respectively, each pool containing products of varying lengths. Sanger sequencing is used to determine sequence. Products are differentiated and separated by molecular weight. The molecular weight of each of the third target products is higher than that of the second target products; the molecular weight of each of the second target products is higher than that of each of the first target products.

In certain embodiments, there can be overlap between the molecular weights of each of the second target products and each of the first target products. Similarly, in certain embodiments, there can be overlap between the molecular weights of each of the third target products and each of the second target products. In some aspects, this sequencing method can be used in connection with any of the embodiments disclosed herein.

In some aspects, the multiplexing sequencing methods are methods for simultaneously analyzing multiple nucleic acid regions in a single reaction, such as those methods disclosed in U.S. Pat. No. 6,197,510, entitled "Multi-loci genomic analysis," the disclosure of which is incorporated herein by reference in its entirety for all purposes.

Allele-Specific Sequencing

In some aspects, sequencing methods are methods for allele-specific sequencing. In particular, in some embodiments, the multiplexing sequencing methods are allele-specific multiplex sequencing (ASMS) methods. Thus, provided are methods, compositions, and systems for allele-specific sequencing, e.g., ASMS, which may be used to determine biomarker and target sequences in connection with the provided methods.

In some embodiments, the ASMS methods are modifications of the Sanger sequencing technology, in which one or more biomarker is sequenced and detected simultaneously with a corresponding sequence not containing the biomarker, e.g., where the biomarker that is a mutant or mutation, in the context of a normal or wild-type sequence, for example, where both sequences are present in the same reaction. In some aspects, the methods are useful for detection of a biomarker present at low copy numbers among a corresponding but different marker, such as a mutant allele present at low copy number among wild-type alleles. In some aspects, the ASMS methods achieve this by designing extension primers, e.g., sequencing primers, which prime extension only from a particular allele or variant, such as a mutant variant, and not from a corresponding other variant, such as a wild-type variant, and using multiple such primers in the same reaction. The primers are also typically designed such that products of their extension may be separated, generally by size or molecular weight, such that the two (or more) sequencing reactions may be carried out in the same reaction volume simultaneously and the products distinguished and identified.

For example, in some aspects, the methods use a plurality of different sequencing primers (e.g., first, second, etc. sequencing primers), each containing at its 3' terminus a nucleotide that pairs with, i.e., is complementary to, the nucleotide present at the corresponding position in either the variant sequence or the normal sequence when hybridized to a polynucleotide containing the variant or wild-type sequence. For example, if a particular genetic variation is characterized by a "T" at a certain position as compared with a "C" in the wild-type or normal sequence, two primers could be used, for example that share identity, but that an "A" and "G," respectively, are present at the nucleotide position of the respective primer that pairs with the corresponding or paired position when hybridized to a polynucleotide containing the variant or wild-type position. In some examples, the primers are otherwise 100% identical, or at least 99, 98, 97, 96, 95, 94, 93, 92, 91, or 90% identical, except for this 3' terminal nucleotide. By virtue of this 3' terminal difference, in some aspects, the first primer primes extension only when paired to a polynucleotide containing the mutant or varied sequence, whereas the second primer primes extension only when paired to a polynucleotide containing the wild-type or normal position. In some aspects, the primers are designed such that one primer is larger in size or molecular weight than all products generated by extension with the other primer, such that products of extension using the two primers can be separated from one another based on size. Thus, sequencing reaction is carried out and multiple different allelic variants of the same locus may be determined simultaneously.

Thus, in certain embodiments, the method includes: (a) combining a first extension primer (e.g., first sequencing primer) a second extension primer (e.g., sequencing primer), a polymerase, and a sample containing a first polynucleotide, a second polynucleotide, or both the first and second polynucleotides, under conditions whereby the first primer is extended by the polymerase when hybridized to the first polynucleotide, thereby producing a pool of first extension products and the second primer is extended by the polymerase when hybridized to the second polynucleotide, thereby producing a pool of second extension products; and (b) differentiating the extension products based on differences in molecular weight. The extension primers typically are sequencing primers.

In some aspects, the first extension primer contains sequence identity to the second extension primer. In some aspects, each of the first and second extension primers is hybridizable to each of the first and second polynucleotides. In some aspects, the 3'-terminal residue of the first extension primer is a first nucleotide, which is complementary to a paired nucleotide in the first polynucleotide when the first extension primer is hybridized to the first polynucleotide. In some aspects, the 3'-terminal residue of the second extension primer is a second nucleotide, which typically is different from the first nucleotide and generally complementary to a paired nucleotide in the second polynucleotide when the second extension primer is hybridized to the second polynucleotide.

In some aspects, the second extension primer has a molecular weight that is greater than that of each of the first extension products. In some aspects, the second extension primer has a molecular weight that is greater than that of the first polynucleotide. In some aspects, the second extension primer has a molecular weight that is at least 1.5, 2, 3, 4, 5, or more times the molecular weight of the first extension primer. In some aspects, the second extension primer is at least 40, 45, 50, 55, 60, 65, 70, 75, 80, 85, 90, or 100 nucleotides in length. In particular embodiments, the first extension products are separated from the second extension products in step (b) based on molecular weight. In certain embodiments, there can be overlap between the molecular weights of the second extension primer and each of the first extension products, or between molecular weights of the second extension primer and the first polynucleotide.

In some embodiments, a third, fourth, and so-forth, extension primer, are used in the method in connection with a third, fourth, and so-forth polynucleotide, whereby third, fourth, etc., extension product pools are produced, with the first, second, third, fourth, etc., extension products separated by molecular weight. In some aspects, the third extension primer has a molecular weight that is greater than that of each of the second extension products; and the fourth extension primer has a molecular weight that is greater than that of each of the third extension products. In some aspects, the third extension primer has a molecular weight that is greater than that of the second polynucleotide; and the fourth extension primer has a molecular weight that is greater than that of the third polynucleotide. In some aspects, the third extension primer has a molecular weight that is at least 1.5, 2, 3, 4, 5, or more times the molecular weight of the second extension primer; and the fourth extension primer has a molecular weight that is at least 1.5, 2, 3, 4, 5, or more times the molecular weight of the third extension primer. In some aspects, the third extension primer is at least 40, 45, 50, 55, typically at least 60, 65, 70, 75, 80, 85, 90, or 100 nucleotides in length.

In some aspects, the allele-specific sequencing method is used in connection with any of the embodiments herein. For example, the target polynucleotide can include an allelic difference or point mutation compared to a corresponding wild-type sequence, and an allele-specific multiplex sequencing (ASMS) method may be used to determine the allelic difference or point mutation comprised in the target polynucleotide. In some embodiments, the method detects the target polynucleotide at a frequency as low as one copy of target polynucleotide per one million copies of a corresponding wild-type sequence.

Figure 9:
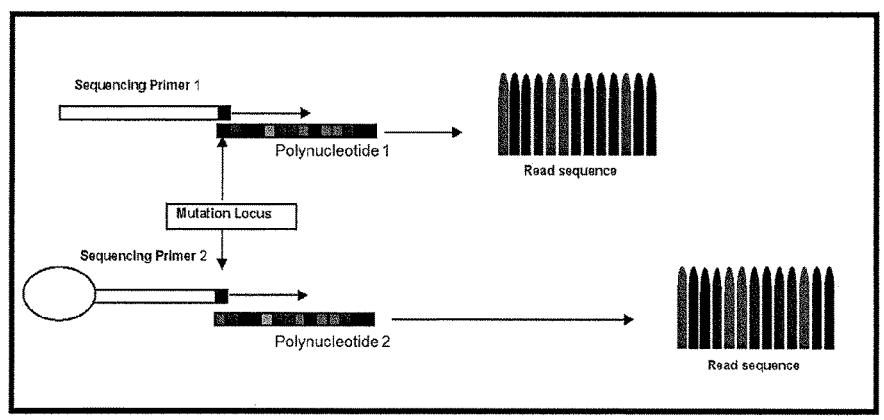
FIG. 9 depicts an allele-specific sequencing process according to an example of the present disclosure and for use with the provided methods. In some aspects, this method is used in connection with the methods shown in one or more of FIGS. 1-8.

For example, as shown in FIG. 9, sequencing primers 1 and 2 are hybridizable to polynucleotides 1 and 2, respectively. When hybridized, the 3'-terminal residue of sequencing primer 1 is complementary to polynucleotide 1, the 3'-terminal residue of sequencing primer 2 is complementary to polynucleotide 2 and is different from that of sequencing primer 1, for example, at the position indicated as "mutation locus." Accordingly, sequencing of polynucleotides 1 and 2 is performed using sequencing primers 1 and 2, respectively. There is no sequencing readout of polynucleotide 1 from sequencing primer 2, or vice versa. As shown in this example, the molecular weight of sequencing primer 2 is higher than that of each of the sequencing products from sequencing primer 1. Accordingly, sequencing products of polynucleotide 1 are separated from those of polynucleotide 2 based on molecular weight. Readout of allele-specific sequences (that of polynucleotide 1 versus polynucleotide 2) can be obtained simultaneously without having to suppress readout from either polynucleotide.

In particular embodiments, the allele-specific multiplex sequencing (ASMS) method is used to detect a plurality of genetic or genomic alterations or variations simultaneously. For example, ASMS allows detection of all three BRAF mutations (V600E, V600D, V600K) without suppressing the wild-type allele and without a need for enrichment of cancer cells. In some aspects, this process is based on use of a first sequencing primer with a nucleotide complementary to a nucleotide within a biomarker in a target polynucleotide at its 3' terminus, and typically a second sequencing primer that contains at a corresponding position a nucleotide that does not pair with the biomarker, i.e., is not complementary to the nucleotide within the biomarker. In some aspects, the second primer is complementary to a wild-type nucleotide. In some aspects, the primers are designed such that the first or second primer has a molecular weight greater than all products generated by the second or first primer, respectively, such that the products can be separated by molecular weight. Thus, in some embodiments, the detection of the wild-type allele serves as an internal control. Accordingly, ASMS generates a verifiable result format. In some embodiments, ASMS achieves a sensitivity of as low as about 1 in 1,000, as low as about 1 in 10,000, as low as about 1 in 100,000, or as low as about 1 in 1,000,000 mutant per wild-type copies. Such features can allow for early detection (Nevi), delivering sensitive and accurate results and reducing costs, for example, by 40%, as compared to available methods.

In some examples, identification includes or is carried out by labeling the target polynucleotide or extended target polynucleotide with a detectable probe, e.g., fluorescent probes, antibody-based probes, or radio-labeled probes. In other aspects, the target polynucleotide or extended target polynucleotide can be identified based on digestion patterns, for example, by restriction enzymes. In some aspects, fragment analysis, e.g., mass spectroscopy or nuclear magnetic resonance imaging, is used.

10. SEQUENCING POLYNUCLEOTIDES

Also provided are sequencing primers for use in connection with the provided methods, and compositions containing the same. For example, in one embodiment, provided is a composition containing two or more sequencing primers, each complementary to two different corresponding biomarkers (e.g., those corresponding to a mutant and wild-type allele of a gene), and each, respectively, containing at its 3' terminus a nucleotide that pairs with, i.e., is complementary to, the nucleotide present at the corresponding position in the respective biomarkers.

For example, if a particular genetic variation is characterized by a "T" at a certain position as compared with a "C" in the wild-type or normal sequence, two primers could be used, for example that share identity, but that an "A" and "G," respectively, are present at the nucleotide position of the respective primer that pairs with the corresponding or paired position when hybridized to a polynucleotide containing the variant or wild-type position. In some examples, the primers are otherwise 100% identical, or at least 99, 98, 97, 96, 95, 94, 93, 92, 91, or 90% identical, except for this 3' terminal nucleotide.

In some aspects, the second extension primer in the composition has a molecular weight that is greater than that of each of the first extension products that could be generated by the first in a sequencing reaction. In some aspects, the second extension primer has a molecular weight that is greater than that of the first polynucleotide, and so forth, for multiple additional primers. In some aspects, the second extension primer has a molecular weight that is at least 1.5, 2, 3, 4, 5, or more times the molecular weight of the first extension primer. In some aspects, the second extension primer is at least 40, 45, 50, 55, 60, 65, 70, 75, 80, 85, 90, or 100 nucleotides in length.

In some aspects, the third extension primer has a molecular weight that is at least 1.5, 2, 3, 4, 5, or more times the molecular weight of the second extension primer; and the fourth extension primer has a molecular weight that is at least 1.5, 2, 3, 4, 5, or more times the molecular weight of the third extension primer. In some aspects, the third extension primer is at least 40, 45, 50, 55, typically at least 60, 65, 70, 75, 80, 85, 90, or 100 nucleotides in length.

11. APPLICATIONS AND USES

Among the provided methods are those providing various advantages over available methods, such as the ability to detect biomarkers present in polynucleotide fragments, including small fragments, in bodily fluids, e.g., at low copy number and/or simultaneously with corresponding wild-type or other corresponding sequences. In some embodiments, the provided methods detect a biomarker or target polynucleotide at a sensitivity of as few as a single (1) copy of the polynucleotide in the sample, or as few as or less than 2, 3 4, 5, 6, 7, 8, 9, 10, 15, 20, 25, 30, 35, 40, 45, or 50 copies of the polynucleotide in the sample, for example, in 1, 2, 3, 4, 5, 6, 7, 8, 9, or 10 mL of sample derived from an individual, e.g., whole blood or plasma. In some aspects, the methods are able to detect or assay a biomarker and/or target polynucleotide at a sensitivity of as low as 1 copy of the target polynucleotide per 1,000, 10,000, 1 100,000, or 1,000,000 total number of polynucleotides in the sample or per 1,000, 10,000, 1 100,000, or 1,000,000 corresponding polynucleotides (e.g., total number of polynucleotides containing identity to or complementarity to the gene, region, or locus of interest or in which the biomarker is found), in the sample or in the sample that do not contain the biomarker of interest, for example, per 1,000, 10,000, 1 100,000, or 1,000,000 corresponding wild-type polynucleotides or polynucleotides not containing the biomarker. In some other aspects, one copy of a target polynucleotide or biomarker can be detected in a sample volume of at least about 1 mL, 2 mL, 3 mL, 4 mL, 5 mL, at least about 10 mL, at least about 15 mL, at least about 20 mL, or more than about 20 mL. For example, in some aspects, one molecule of a target polynucleotide in about 10 mL to 15 mL of blood can be detected using the method disclosed herein.

In some aspects, detection, identification, and/or determining the presence of the biomarker or target polynucleotide provides diagnostic and/or prognostic information about a disease, disorder, condition, or stage or state thereof, for example, in a subject from which the sample, e.g., biological sample is taken. For example, in some aspects, the detection, determination, or identification of the target polynucleotide or biomarker in the sample determines the presence, absence severity, prognosis, stage, or other information about a disease, condition, or other event.

In some aspects, the disease, condition, disorder, and/or event can include but is not limited to cancer, tumor, metastasis, malignancy, proliferative disease or disorder, prenatal or fetal condition, genetic predisposition, hereditary disease or condition, genetic defect, congenital disease or condition, pregnancy or complication thereof, autoimmune or inflammatory disease or condition, cardiovascular disease or condition, CNS disease or condition, metabolic disease or condition, transplant acceptance or rejection, or likelihood of success or treatment outcome using a particular therapy or treatment, such as drug, biologic, surgery, device, transplantation, intervention, or other treatment, in or by the subject from which the biological sample is taken.

Among the tumors and cancers are blood-based cancers, such as leukemia and lymphoma, such as Hodgkin and non-Hodgkin lymphoma, solid tumors, colorectal cancer, gastrointestinal cancer, stomach cancer, prostate cancer, liver cancer, lung cancer, bone cancer, pancreatic cancer, bladder cancer, ovarian cancer, breast cancer, melanoma, papillary thyroid carcinoma, non-small cell lung carcinoma, adenocarcinoma of lung, papillary thyroid carcinomas, gastrointestinal stromal tumors. Among the cancers are malignant cancers, and primary and metastasized cancers and tumors.

Among the inflammatory diseases and conditions are arthritis, e.g., rheumatoid arthritis, allergy, asthma, multiple sclerosis, hypersensitivity, pruritus, colitis, e.g., ulcerative colitis, inflammatory bowel disease, Crohn's disease, lupus, muscular dystrophy, septic shock and septicemia.

Among the cardiovascular diseases and conditions are atherosclerosis, restenosis, myocardial infarction, congestive heart failure, cardiomyopathy, defects in heart function, coronary, carotid, and cerebral lesions, cardiac ischemia, and other heart diseases and disorders.

In some aspects, the methods are useful as part of a treatment or therapeutic method for the disease, disorder, or condition. For example, in some embodiments, detection of the presence or absence of the biomarker in the sample or subject indicates the success or likelihood of success of a particular treatment, e.g., drug or surgical intervention. For example, where the biomarker is high expression of a particular gene product or a genetic variation, such as a mutation in a particular gene, the method may indicate that a treatment specifically targeting that gene is likely to treat the subject in which the biomarker has been identified. Thus, in some embodiments, provided are methods of treatment, carried out by detecting the presence or absence one or more biomarkers in a sample derived from a subject as described herein, where the detection of the presence or absence of the biomarker indicates that a treatment is likely to be successful or is not likely to be successful in treating the subject. In some aspects, the methods further include administering a treatment to the subject, such as the treatment which it is determined is likely to be successful in treating the subject. In some aspects, the methods further include discontinuing or altering the treatment of the subject, for example, discontinuing treatment that it is deemed is unlikely to treat the subject, for example, in favor of a more appropriate treatment.

In particular examples, the biomarkers include or are a BRAF gene or gene product and/one or more mutations in the BRAF gene. The BRAF gene encodes a serine/threonine protein kinase that regulates the MAPK/ERK signaling pathways, affecting cell growth and proliferation. BRAF somatic mutations are observed in cancers, including non-Hodgkin lymphoma, colorectal cancer, malignant melanoma, papillary thyroid carcinoma, non-small cell lung carcinoma, and adenocarcinoma of lung. In particular, BRAF mutations are associated with approximately 10% of human colorectal cancers, approximately 45% of papillary thyroid carcinomas, about 50% of melanomas, and about 5-10% of gastrointestinal stromal tumors (GIST). BRAF mutations include V600E and V600D, and BRAF mutation 1799T>A (V600E) is the most common (about 85% of all BRAF mutations).

In some aspects, the disease or condition or disorder or event is one that is associated with disintegrated DNA fragments in a biological sample, e.g., extracellular biological sample, e.g., bodily fluid, e.g., blood, of a subject having the disease, disorder, or condition. Elevated levels of extracellular nucleic acids such as DNA and/or RNA are present in many conditions including but not limited to malignancies, infections, autoimmune and inflammatory diseases and conditions, and pregnancy. For example, elevated fetal DNA or RNA in maternal blood can be used to determine gender identity, assess chromosomal abnormalities, and monitor pregnancy-associated complications, among uses. In addition, a biological sample may also include other polynucleotides of interest, including pathogen nucleic acids such as viral nucleic acids. In such examples, a viral or pathogenic nucleic acid may or may not be integrated into the genome of a cell of the subject from which the biological sample is obtained.

In some examples, the methods are used to detect the presence of antisense oligonucleotides, including those administered as disease treatments, such as may be useful in determining or confirming the dosage or half-life of antisense treatments. Thus, the provided methods in some contexts determine or confirm or analyze the pharmacodynamics, pharmacokinetics, serum half-life, delivery, or other aspect of an antisense oligonucleotide treatment.

Extracellular target polynucleotides and their detection and assaying by the provided methods are used in some embodiments to extract clinical information for use in early diagnosis, prevention and management of diseases and other conditions. Identification and assaying of extracellular target polynucleotides are particularly useful in some embodiments in non-invasive diagnosis and prognosis, for example, as markers in many fields of application, such as non-invasive oncology testing, prenatal genetic testing, transplantation, autoimmune diseases, screening for genetic defects, and personalized medicine.

Applications and analysis methods of extracellular polynucleotides are described, for example, in Hromadnikova, et al., 2006, *DNA Cell Biol* 25:635-640; Fleischhacker, 2006, *Ann. N.Y. Acad Sci.* 1075:40-49; Fleischhacker and Schmidt, 2007, *Biochmica et Biophysica Acta* 1775:191-232; Swarup, et al., 2007, *FEBS Letters* 581:795-799; Fan, et al., 2010, *Clinical Chemistry* 56:1279-1286; WO1997/035589; WO1997/034015; U.S. Pat. Nos. 5,496,699; 5,512,441; 5,952,170; 6,156,504; 6,329,179; 6,521,409; 6,630,301; 6,759,217; 6,916,634; 6,939,671; 6,939,675; 7,282,335; 7,829,285; and 7,811,752, the disclosures of which are incorporated herein by reference in their entirety for all purposes.

The following examples are intended to further describe and illustrate various aspects of the disclosure, but not to limit, the scope of the disclosure in any manner, shape, or form, either explicitly or implicitly.

Example 1 Detection of Synthetic Target Polynucleotides

This example demonstrates detection of polynucleotide fragments in a liquid sample. In this particular example, the polynucleotide fragments (target polynucleotides) were synthesized and provided in a sample. The following polynucleotides were ordered from and synthesized by IDT (Integrated DNA Technologies, USA).

```
Template polynucleotide:
                                        (SEQ ID NO: 1)
5'-CCTCAATTCTTACCATCCACAAAATGGATCCAGACAACTGTTCAA

ACTGATGGGACCCACTCCATCGAGATTTCACTGTAGCTAGACCAAAAT

CACCTATTTTTACTGTGAGGTC-3'

Synthetic target polynucleotide 1
(BRAF V600E mutant fragment 1):
                                        (SEQ ID NO: 2)
5'GACCTCACATGTAAAATAGGTGATTTTGGTCTAGCTACAGAGAAAT

C-3'

Synthetic target polynucleotide 2
(BRAF V600E mutant fragment 2):
                                        (SEQ ID NO: 3)
5'-TTTTGGTCTAGCTACAGAGAAATCTCGATGGAGTGGGTCCCATCA

GTTTGAACAGT-3'

Synthetic target polynucleotide 3
(BRAF wild-type fragment):
                                        (SEQ ID NO: 4)
5'-TTTTGGTCTAGCTACAGTGAAATCTCGATGGAGTGGGTCCCATCA

GTTTGAACAGT-3'

Amplification primer:
                                        (SEQ ID NO: 5)
5'-CAATTCTTACCATCCACAAAATGGATCCAG-3'

BRAF V600E mutant sequencing primer:
                                        (SEQ ID NO: 6)
5'-AAACTGATGGGACCCACTCCATCGAGATTTCT-3'

BRAF wild-type sequencing primer:
                                        (SEQ ID NO: 7)
51-AAACTGATGGGACCCACTCCATCGAGATTTCA-3'.
```

In some examples, a template polynucleotide corresponding to the BRAF V600E mutant sequence is provided:

```
                                        (SEQ ID NO: 8)
5'-CCTCAATTCTTACCATCCACAAAATGGATCCAGACAACTGTTCAA

ACTGATGGGACCCACTCCATCGAGATTTCTCTGTAGCTAGACCAAAAT

CACCTATTTTTACTGTGAGGTC-3'.
```

Each of the synthetic target polynucleotides 1-3 (SEQ ID NOS:2-4, respectively) aligns with and contains complementarity to, and thus hybridizes to, both the wild-type and the V600E template polynucleotides (SEQ ID NOS:1 and 8, respectively), although there is a single nucleotide mismatch between the wild type template and mutant targets, and vice versa.

For example, the wild-type synthetic template polynucleotide (SEQ ID NO:1) contained a wild-type BRAF sequence, and aligned with and contained 100% complementarity to the sequence of synthetic target polynucleotide 3 (BRAF wild-type fragment, SEQ ID NO:4) as shown in FIG. 10A. The bolded nucleotides, e.g., in FIG. 10A, in SEQ ID NOS:1 and 4 are part of a codon encoding V600 (valine 600) in wild-type BRAF.

Likewise, synthetic target polynucleotide 1 (BRAF V600E mutant fragment 1, SEQ ID NO:2) aligned with and contained 100% complementarity to a template polynucleotide corresponding to a BRAF V600E mutant sequence (SEQ ID NO:8) as shown in FIG. 10B. The bolded nucleotides, e.g., in FIG. 10B, in SEQ ID NOS:2 and 8 are part of a codon encoding E600 (glutamate 600) in the V600E BRAF mutant. Synthetic target polynucleotide 2 (BRAF V600E mutant fragment 2, SEQ ID NO:3) aligned with and contained complementarity to the template polynucleotide of SEQ ID NO:8 as shown in FIG. 10C. The bolded nucleotides, e.g., in FIG. 10C, in SEQ ID NOS:3 and 8 are part of a codon encoding E600 (glutamate 600) in the V600E BRAF mutant.

An amplification primer (SEQ ID NO:5) was homologous to the 5' end of the template polynucleotide SEQ ID NO:1 and the 5' end of the template polynucleotide of SEQ ID NO:8, and was thus hybridizable to the 3' end of extended target polynucleotides generated by extension of synthetic target polynucleotides 1-3 (SEQ ID NOS:2-4, respectively), upon hybridization to either template and subjected to primer extension based on the template sequences. The BRAF V600E mutant sequencing primer (SEQ ID NO:6) carried the mutant nucleotide "T" at its 3' end (bolded), which is part of a codon encoding E600 in the V600E BRAF mutant. The BRAF wild-type sequencing primer (SEQ ID NO:7) carried the wild-type nucleotide "A" at its 3' end (bolded), which is part of a codon encoding V600 in wild-type BRAF.

Reactions to extend the target polynucleotides were set up in 50 µl total volumes, using Qiagen® Multiplex PCR plus kit (Qiagen, USA Cat No. 206152). Four reactions were carried out to generate and amplify extended target polynucleotides.

For a first reaction, 25 µl Qiagen® PCR buffer was mixed with 5 µl Q-Solution (to promote efficient amplification of GC rich templates), 1 µl target polynucleotide 1 (SEQ ID NO:2) at a concentration of 10 pmol/µl, 1 µl template polynucleotide (SEQ ID NO:1) at a concentration of 10 pmol/µl, 5 µl amplification primer (SEQ ID NO:5) at a concentration of 100 pmol/µl, and 13 µl water.

For a second reaction, 25 µl Qiagen® PCR buffer was mixed with 5 µl Q-Solution, 1 µl target polynucleotide 2 (SEQ ID NO:3) at a concentration of 10 pmol/µl, 1 µl template polynucleotide (SEQ ID NO:1) at a concentration of 10 pmol/µl, 5 µl amplification primer (SEQ ID NO:5) at a concentration of 100 pmol/µl, and 13 µl water.

For a third reaction, 25 µl Qiagen® PCR buffer was mixed with 5 µl Q-Solution, 1 µl target polynucleotide 3 (SEQ ID NO:4) at a concentration of 10 pmol/µl, 1 µl template polynucleotide (SEQ ID NO:1) at a concentration of 10 pmol/µl, 5 µl amplification primer (SEQ ID NO:5) at a concentration of 100 pmol/µl, and 13 µl water.

For a fourth reaction, 25 µl Qiagen® PCR buffer was mixed with 5 µl Q-Solution, 3 µl target polynucleotide mixture containing 1 µl each of synthetic target polynucleotides 1-3 (SEQ ID NOS:2-4, respectively) at a concentration of 10 pmol/µl, 1 µl template polynucleotide (SEQ ID NO:1) at a concentration of 10 pmol/µl, 5 µl amplification primer (SEQ ID NO:5) at a concentration of 100 pmol/µl, and 11 µl water.

For all four reactions, the reaction mixtures were held at 95° C. for 5 seconds, subjected to 35 reaction cycles (95° C. for 30 seconds, 54° C. for 90 seconds, and 72° C. for 30 seconds), and held at 68° C. for 10 seconds. The reaction mixture containing the resulting extended target polynucleotides was then held at 4° C. before purification.

The extended target polynucleotides and amplified copies thereof generated by extension of synthetic target polynucleotides 1-3 and amplification in the four reactions were then purified using the AMPure® system (Agencourt Bioscience, Beverly, Mass.).

Purified extended target polynucleotides were sequenced using the BRAF V600E mutant sequencing primer (SEQ ID NO:6) and the BRAF wild-type sequencing primer (SEQ ID NO:7) by cycle sequencing using the ABI PRISM® BigDye® Terminator Cycle Sequencing Ready Reaction Kit version 1.1 (Applied Biosystems, USA) on a GeneAmp® 2400 thermocycler (PE Applied Biosystems, USA). The sequencing reaction was performed in 10 µl total volumes. In one experiment, 3.5 µl 5× sequencing buffer was mixed with 1 µl BigDye®, 1 µl BRAF wild-type sequencing primer (SEQ ID NO:7) at a concentration of 3.3 pmol/µl, 1.5 µl BRAF V600E sequencing primer (SEQ ID NO:6) at a concentration of 3.3 pmol/µl, 8 µl purified extended target polynucleotides, and 5 µl water. The sequencing reaction mixtures were subjected to 25 reaction cycles (96° C. for 15 seconds, 55° C. for 8 seconds, and 60° C. for 2.5 minutes). Unincorporated dye terminators were removed using CleanSEQ® system (Agencourt Bioscience, Beverly, Mass.). The sequencing reaction mixtures were then analyzed by capillary electrophoresis using the ABI PRISM® Genetic Analyzer 3130 (Applied Biosystems, USA). In the respective sequencing reactions from each of the four extension and amplification reactions, sequencing products specific for wild-type BRAF, the BRAF V600E mutation, or both, were detected.

In another example, the extension and amplification reactions above are carried out using a template of SEQ ID NO:8, to detect each of the target polynucleotides 1-3 in a sample or samples.

Example 2 Detection of Target Polynucleotides in Urine Samples

This example demonstrates detection of polynucleotide fragments, and biomarkers contained therein, spiked into urine samples A 50 µl cocktail was made by mixing 10 µl of target polynucleotide 1, 10 µl of target polynucleotide 2, 10 µl of target polynucleotide 3, and 20 µl of DNase-free water. 25 µl of the cocktail was used to spike 1 mL of a urine sample from a normal individual. The spiked urine sample was then micro-centrifuged at 13,000 rpm in an Eppendorf™ centrifuge, and the supernatant was discarded. 800 µl of 10% PBS was added to the Eppendorf™ tube, and the pellet was resuspended by vortexing. The Eppendorf™ tube was then centrifuged again and the supernatant was discarded. The pellet was then resuspended in 15 µl of TE buffer.

Three (3) µl of the TE buffer with resuspended pellet was then used in extension reactions with 50 µl total volumes to extend the target polynucleotides. 25 µl Qiagen® PCR buffer was mixed with 5 µl Q-Solution, 3 µl of the TE buffer with resuspended pellet, 1 µl template polynucleotide (SEQ ID NO:1) at a concentration of 10 pmol/µl, 5 µl amplification primer (SEQ ID NO:5) at a concentration of 100 pmol/µl, and 11 µl water. The reaction mixtures were held at 95° C. for 5 seconds, subjected to 35 reaction cycles (95° C. for 30 seconds, 54° C. for 90 seconds, and 72° C. for 30 seconds), and held at 68° C. for 10 seconds. The reaction mixture containing the extended target polynucleotides was then held at 4° C. before purification.

The extended target polynucleotides (including amplified copies thereof) generated by extension of the target polynucleotides 1-3 (and amplification thereof) in reactions derived from the spiked urine sample were then purified using the AMPure™ system (Agencourt Bioscience, Beverly, Mass.). Purified extended target polynucleotides were sequenced using the BRAF V600E mutant sequencing primer (SEQ ID NO:6) and the BRAF wild-type sequencing primer (SEQ ID NO:7) by cycle sequencing using the ABI PRISM® BigDye® Terminator Cycle Sequencing Ready Reaction Kit version 1.1 (Applied Biosystems, USA) on a GeneAmp® 2400 thermocycler (PE Applied Biosystems, USA). The sequencing reaction was performed in 10 µl total volumes. 3.5 µl 5× sequencing buffer was mixed with 1 µl BigDye®, 1 µl BRAF wild-type sequencing primer (SEQ ID NO:7) at a concentration of 3.3 pmol/µl, 1.5 µl BRAF V600E sequencing primer (SEQ ID NO:6) at a concentration of 3.3 pmol/µl, 8 µl purified extended target polynucleotides, and 5 µl water. The sequencing reaction mixture was subjected to 25 reaction cycles (96° C. for 15 seconds, 55° C. for 8 seconds, and 60° C. for 2.5 minutes). Unincorporated dye terminators were removed using CleanSEQ® system (Agencourt Bioscience, Beverly, Mass.). The sequencing reaction mixture was then analyzed by capillary electrophoresis using the ABI PRISM® Genetic Analyzer 3130 (Applied Biosystems, USA). Sequencing products containing the wild-type BRAF and the BRAF V600E mutation biomarkers were detected, thereby identifying the biomarkers in the urine sample and the sample derived from it.

Example 3 Detection of Target Polynucleotides in Human Blood Plasma Samples

This example demonstrates detection of polynucleotide fragments, and biomarkers contained therein, spiked into human blood plasma samples. A 50 µl cocktail was made by mixing 10 µl of target polynucleotide 1, 10 µl of target polynucleotide 2, 10 µl of target polynucleotide 3, and 20 µl of DNase-free water. 25 µl of the cocktail was used to spike 1 mL of a human blood plasma sample from a normal individual. The spiked human blood plasma sample was then micro-centrifuged at 13,000 rpm in an Eppendorf™ centrifuge, and the supernatant was discarded. 800 µl of 10% PBS was added to the Eppendorf™ tube, and the pellet was resuspended by vortexing. The Eppendorf™ tube was then centrifuged again and the supernatant was discarded. The pellet was then resuspended in 15 µl of TE buffer.

Three (3) µl of the TE buffer with resuspended pellet was then used in reactions with 50 µl total volumes to extend and amplify the target polynucleotides, generated extended target polynucleotides containing the biomarkers.

Twenty-five (25) µl Qiagen® PCR buffer was mixed with 5 µl Q-Solution, 3 µl of the TE buffer with resuspended pellet, 1 µl template polynucleotide (SEQ ID NO:1) at a concentration of 10 pmol/µl, 5 µl amplification primer (SEQ ID NO:5) at a concentration of 100 pmol/µl, and 11 µl water. The reaction mixtures were held at 95° C. for 5 seconds, subjected to 35 reaction cycles (95° C. for 30 seconds, 54° C. for 90 seconds, and 72° C. for 30 seconds), and held at 68° C. for 10 seconds. The reaction mixture containing the extended target polynucleotides was then held at 4° C. before purification.

The extended target polynucleotides (including amplified copies thereof), generated by extension of synthetic target polynucleotides 1-3 in the spiked human blood plasma sample were then purified using the AMPure® system (Agencourt Bioscience, Beverly, Mass.). Purified extended target polynucleotides were sequenced using the BRAF V600E mutant sequencing primer (SEQ ID NO:6) and the BRAF wild-type sequencing primer (SEQ ID NO:7) by cycle sequencing using the ABI PRISM® BigDye® Terminator Cycle Sequencing Ready Reaction Kit version 1.1 (Applied Biosystems, USA) on a GeneAmp® 2400 thermocycler (PE Applied Biosystems, USA). The sequencing reaction was performed in 10 µl total volumes. In one experiment, 3.5 µl 5× sequencing buffer was mixed with 1 µl BigDye®, 1 µl BRAF wild-type sequencing primer (SEQ ID NO:7) at a concentration of 3.3 pmol/µl, 1.5 µl BRAF V600E sequencing primer (SEQ ID NO:6) at a concentration of 3.3 pmol/µl, 8 µl purified extended target polynucleotides, and 5 µl water. The sequencing reaction mixtures were subjected to 25 reaction cycles (96° C. for 15 seconds, 55° C. for 8 seconds, and 60° C. for 2.5 minutes). Unincorporated dye terminators were removed using CleanSEQ® system (Agencourt Bioscience, Beverly, Mass.). The sequencing reaction mixtures were then analyzed by capillary electrophoresis using the ABI PRISM® Genetic Analyzer 3130 (Applied Biosystems, USA). Sequencing products specific for wild-type BRAF biomarker and the BRAF V600E mutation biomarker, respectively, were detected, thereby identifying the presence of the biomarkers in the blood plasma sample and the sample derived from it.

All headings are for the convenience of the reader and should not be used to limit the meaning of the text that follows the heading, unless so specified. It should be understood that the various features described in one or more of the individual embodiments are not limited in their applicability to the particular embodiment with which they are described. The breadth and scope of the present disclosure should not be limited by any of the above-described exemplary embodiments.

Citation of the above publications or documents is not intended as an admission that any of them is pertinent prior art, nor does it constitute any admission as to the contents or date of these publications or documents.

| Sequence Listing | |
|---|---|
| SEQ ID NO | Sequence |
| SEQ ID NO: 1 | 5'-CCTCAATTCTTACCATCCACAAAATGGATCCAGACAACTGTTCAAACTGATGGGACCCACTCCATCGAGATTTCACTGTAGCTAGACCAAAATCACCTATTTTTACTGTGAGGTC-3' |
| SEQ ID NO: 2 | 5'-GACCTCACATGTAAAATAGGTGATTTTGGTCTAGCTACAGAGAAATC-3' |
| SEQ ID NO: 3 | 5'-TTTTGGTCTAGCTACAGAGAAATCTCGATGGAGTGGGTCCCATCAGTTTGAACAGT-3' |
| SEQ ID NO: 4 | 5'-TTTTGGTCTAGCTACAGTGAAATCTCGATGGAGTGGGTCCCATCAGTTTGAACAGT-3' |
| SEQ ID NO: 5 | 5'-CAATTCTTACCATCCACAAAATGGATCCAG-3' |
| SEQ ID NO: 6 | 5'-AAACTGATGGGACCCACTCCATCGAGATTTCT-3' |
| SEQ ID NO: 7 | 5'-AAACTGATGGGACCCACTCCATCGAGATTTCA-3' |
| SEQ ID NO: 8 | 5'-CCTCAATTCTTACCATCCACAAAATGGATCCAGACAACTGTTCAAACTGATGGGACCCACTCCATCGAGATTTCTCTGTAGCTAGACCAAAATCACCTATTTTTACTGTGAGGTC-3' |

The invention claimed is:

1. A method comprising:
   (a) hybridizing at a 3' end of a target polynucleotide that carries a biomarker of interest; the 3' end of the target polynucleotide being complementary to a 3' end of a template polynucleotide wherein both 3' ends will hybridize to each other forming a partial nucleic acid duplex at the 3' ends;
   while hybridizing at the 3' ends, leaving free:
      a 5' end of the target polynucleotide, and
      a 5' end of the template polynucleotide,
   (b) creating an extended nucleic acid duplex by:
      providing a polymerase under conditions that permit extension of the 3' end of the template polynucleotide towards the 5' end of the target polynucleotide thereby producing an extended template polynucleotide, and that permit extension of the 3' end of the target polynucleotide thereby producing an extended target polynucleotide complementary to the 5' end of the template polynucleotide; and
   (c) amplifying the extended nucleic acid duplex using a first primer that hybridizes at the 5' end of an extended portion of the target polynucleotide and a second primer that hybridizes to an extended portion of the template polynucleotide to form an amplicon.

2. The method of claim 1 wherein the target polynucleotide is naturally occurring.

3. The method of claim 1 wherein the target polynucleotide comprises a plurality of target polynucleotides, each comprising the biomarker of interest.

4. The method of claim 1 wherein the amplicon produced is subsequently sequenced to determine a nucleotide sequence of the target polynucleotide.

5. The method of claim 1 wherein an extended target polynucleotide sequence comprises a portion complementary to the 5' end of the template polynucleotide and a portion complementary to the 5' end of the of the target polynucleotide.

6. The method of claim 1 further comprising sequencing at least a segment of the target polynucleotide using a sequencing primer that anneals at any part of the target polynucleotide generating a nucleotide sequence from a 3' end of the sequencing primer that is complementary to the target polynucleotide.

7. The method of claim 1 wherein the target polynucleotide is a nucleic acid polymer selected from the group consisting of a single stranded DNA fragment, a double stranded DNA fragment, and a RNA segment.

8. The method of claim 1 wherein the target polynucleotide is between 25 and 200 nucleotides in length.

* * * * *